US008802156B2

(12) United States Patent
Franco Rodriguez et al.

(10) Patent No.: US 8,802,156 B2
(45) Date of Patent: Aug. 12, 2014

(54) PHARMACEUTICAL FORMS FOR THE RELEASE OF ACTIVE COMPOUNDS

(75) Inventors: Guillermo Franco Rodriguez, Madrid (ES); Ibon Gutierro Aduriz, Granada (ES)

(73) Assignee: Laboratorios Farmacéuticos Rovi, S.A., Madrid (ES)

(*) Notice: Subject to any disclaimer, the term of this patent is extended or adjusted under 35 U.S.C. 154(b) by 140 days.

(21) Appl. No.: 13/193,977

(22) Filed: Jul. 29, 2011

(65) Prior Publication Data

US 2012/0022020 A1 Jan. 26, 2012

Related U.S. Application Data

(63) Continuation-in-part of application No. 12/779,556, filed on May 13, 2010, now Pat. No. 8,257,744, which is a continuation-in-part of application No. PCT/EP2008/065499, filed on Nov. 13, 2008, application No. 13/193,977, which is a continuation-in-part of application No. PCT/EP2010/051127, filed on Jan. 29, 2010.

(30) Foreign Application Priority Data

Nov. 14, 2007 (EP) .................................. 07380319
Jan. 30, 2009 (EP) .................................. 09382014

(51) Int. Cl.
*A61K 9/16* (2006.01)
*A61K 9/20* (2006.01)

(52) U.S. Cl.
CPC ............. *A61K 9/2027* (2013.01); *A61K 9/2072* (2013.01)
USPC ............................ 424/497; 424/489; 424/490

(58) Field of Classification Search
CPC ........... A61K 9/08; A61K 9/14; A61K 9/127; A61K 9/141; A61K 9/1617; A61K 9/1629
USPC ........................................ 424/465–489, 497
See application file for complete search history.

(56) References Cited

U.S. PATENT DOCUMENTS

| | | | |
|---|---|---|---|
| 3,482,014 | A | 12/1969 | Koh |
| 4,703,042 | A | 10/1987 | Bodor |
| 5,151,273 | A | 9/1992 | Korsatko-Wabnegg et al. |
| 5,490,990 | A | 2/1996 | Grabowski et al. |
| 5,622,657 | A | 4/1997 | Takada et al. |
| 5,629,011 | A | 5/1997 | Illum |
| 5,639,469 | A | 6/1997 | Benes |
| 5,686,113 | A | 11/1997 | Speaker et al. |
| 5,849,327 | A | 12/1998 | Berliner |
| 5,900,252 | A | 5/1999 | Calanchi |
| 6,248,363 | B1 | 6/2001 | Patel |
| 6,458,383 | B2 | 10/2002 | Chen |
| 6,475,493 | B1 | 11/2002 | Mulye |
| 6,677,318 | B1 | 1/2004 | Beisel |
| 6,692,771 | B2 | 2/2004 | Pather |
| 6,919,091 | B2 | 7/2005 | Trubetskoy |
| 7,393,840 | B2 | 7/2008 | Rosenberg |
| 7,674,767 | B2 | 3/2010 | Pai et al. |
| 8,052,998 | B2 | 11/2011 | Maincent et al. |
| 2001/0024658 | A1 | 9/2001 | Chen |
| 2002/0160049 | A1 | 10/2002 | Pather |
| 2003/0044458 | A1* | 3/2003 | Wright et al. ................. 424/458 |
| 2003/0091623 | A1 | 5/2003 | Cumming |
| 2003/0161884 | A1* | 8/2003 | Rosenberg et al. ........... 424/486 |
| 2003/0198619 | A1 | 10/2003 | Dong |
| 2005/0013866 | A1 | 1/2005 | Maincent et al. |
| 2005/0020539 | A1 | 1/2005 | Ajani et al. |
| 2006/0018933 | A1 | 1/2006 | Vaya |
| 2006/0018934 | A1 | 1/2006 | Vaya |
| 2006/0024365 | A1 | 2/2006 | Vaya |
| 2007/0154559 | A1 | 7/2007 | Pai |
| 2008/0275001 | A1 | 11/2008 | Cumming |
| 2010/0316722 | A1 | 12/2010 | Lopez-Belmonte Encina et al. |

FOREIGN PATENT DOCUMENTS

| | | |
|---|---|---|
| EP | 1652836 A1 | 5/2006 |
| FR | 2769853 | 4/1999 |
| WO | WO92/11844 | 7/1992 |
| WO | WO9414420 | 7/1994 |
| WO | WO96/28143 | 9/1996 |
| WO | WO/0028989 | 5/2000 |
| WO | WO/0043044 | 7/2000 |
| WO | 02/03960 A1 | 1/2002 |
| WO | 2005/032703 A1 | 4/2005 |
| WO | 2007/079252 A2 | 7/2007 |

OTHER PUBLICATIONS

Gangwar ("Prodrug strategies to enhance intestinal absorption of peptides") Drug Discovery Today (1997), 2(4), pp. 148-155.
Whitehead ("Oral delivery of macromolecules using intestinal patches: applications for insulin delivery") J. Control. Rel. (2004), 98(1), pp. 37-45.
Hoffart ("Oral bioavailability of a low molecular weight heparin using a polymeric delivery system") J. Control. Rel. (2006), 113(1), pp. 38-42.
Jiao ("Anticoagulant activity of heparin following oral administration of heparin-loaded microparticles in rabbits") J. Pharm. Sci. (2002), 91(3), pp. 760-768.
Leone-Bay ("Acylated non-alpha-amino acids as novel agents for the oral delivery of heparin sodium") J. Control. Rel. (1998), 50(1-3), pp. 41-49.
Kim ("Oral delivery of chemical conjugates of heparin and deoxycholic acid in aqueous formulation") Thromb. Res. (2006), 117(4), pp. 419-427.
Hoffart et al. ("Oral bioavailability of a low molecular weight heparin using a polymeric delivery system") J. Control. Rel. (2006), 113(1), pp. 38-42.

\* cited by examiner

*Primary Examiner* — Michael G Hartley
*Assistant Examiner* — Micah-Paul Young
(74) *Attorney, Agent, or Firm* — Rick Matos; Innovar, L.L.C.

(57) ABSTRACT

A pharmaceutical composition containing a sulfated glycosaminoglycan drug and a polycationic polymer or copolymer wherein the proportion of ammonium groups in the pharmaceutical composition is between 0.01-2.0 μmol ammonium groups/mg pharmaceutical composition, the proportion of glycosaminoglycan in the pharmaceutical form is between 15% to 50% w/w, and the pharmaceutical composition possesses a moisture content of 10% wt or less. A pharmaceutical dosage form containing the pharmaceutical composition, and their use for the treatment of diseases or disorders therapeutically responsive to the glycosaminoglycan.

66 Claims, 19 Drawing Sheets

PHARMACEUTICAL FORMS FOR THE RELEASE OF ACTIVE COMPOUNDS

CROSS-REFERENCE TO EARLIER FILED APPLICATIONS

The present application claims the benefit of and is a continuation-in-part of U.S. Ser. No. 12/779,556 filed May 13, 2010, which is a continuation-in-part of PCT International Application No. PCT/EP2008/065499, filed Nov. 13, 2008, which claims the benefit of European Application No. 07380319.9, filed Nov. 14, 2007; and the present application also claims the benefit of and is a continuation-in-part of PCT International Patent Application No. PCT/EP2010/051127 filed Jan. 29, 2010, which claims the benefit of European Application No. 09382014.0 filed Jan. 30, 2009.

FIELD OF THE INVENTION

The present invention relates to pharmaceutical compositions for the delivery and release of glycosaminoglycans (GAG) for absorption by mucosa following administration thereof, as well as to pharmaceutical formulations containing said pharmaceutical compositions and to the use of said pharmaceutical compositions and formulations for the manufacture of a medicament suitable for application to mucosa. The invention also provides a method of treating a disease or disorder with the composition or dosage form.

BACKGROUND OF THE INVENTION

Numerous active compounds cannot be administered orally for a variety of reasons including: a) their rapid enzymatic and metabolic degradation; b) their chemical and biological instability; c) their low solubility in aqueous medium, and/or d) their limited permeability in the gastrointestinal tract.

Exemplary active compounds presenting one or more these problems include glycosaminoglycan (GAG)-type macromolecules, such as heparin and its derivatives, LMWH (Low Molecular Weight Heparins), pentasacharides (like fondaparinux), ULMWH (Ultra Low Molecular Weight Heparins), Chondroitin sulfate, Dermatan sulfate, etc. GAG-type macromolecules are highly sulfated un-branched polysaccharides that comprise repeating disaccharides of an uronic acid (iduronic or glucuronic) linked to an aminosugar (glucosamine or galactosamine). The building blocks of these macromolecules are as follows:

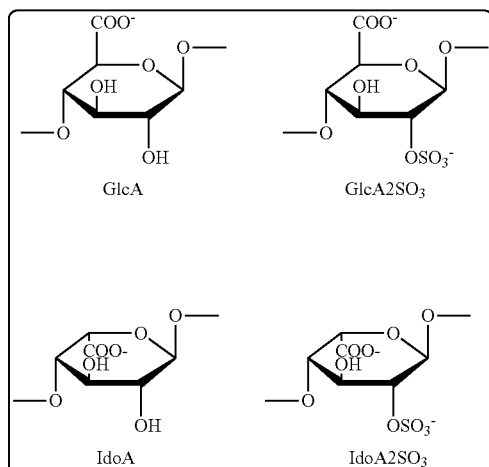

Uronic Acids

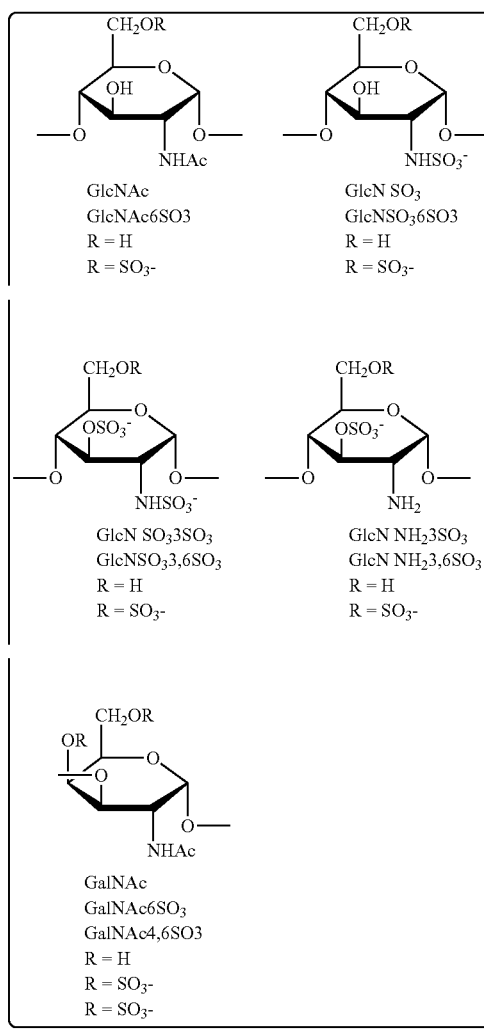

Aminosugars

Determining the content of sulfate and uronic groups is essential in order to evaluate the charge distribution along the polyelectrolyte chain. Conductimetry provides a simple and rapid method for determining the absolute content of both of sulfate and carboxyl groups in glycosminoglicans (GAGs), since, conductimetric curves obtained by titrating the acid form of a GAG with a strong base are characteristic of the GAG ("A conductimetry method for the determination of sulfate and carboxyl groups in heparin and other muopolysaccharides. Benito Casu and Ugo Genaro". *Carbohydrate Research* (1975), 39, 168-179). Using this methodology sulfate and carboxyl group percentages in different GAGs has been determined:

| GAG | SO3-% dry substance weight | COO-% dry substance weight |
| --- | --- | --- |
| Unfractionated heparin | 25-35% | 7-8% |
| Low Molecular Weight Heparin | 25-29% | 6-7% |
| Chondroitin Sulfate | 11-17% | 6-9% |
| Dermatan Sulfate | 15-20% | 5-8% |
| Fondaparinux | 37% | 5% |

These GAG-type macromolecules are very important for treating different diseases, for example, low molecular weight heparins (LMWH) are the standard anticoagulant used in the prevention and treatment of deep vein thrombosis and pulmonary embolism (Ageno 2000 "Treatment of venous thromboembolism." *Thromb Res* (2000) 97(1): V63-72; Agnelli, G. and F. Sonaglia. "Prevention of venous thromboembolism." *Thromb Res* (2000) 97(1): V49-62.). For many years, LMWH have been used more than unfractionated heparin (UFH) in many countries due to the decrease of health care cost and their simple utilization (Kakkar, A. K. "Low- and ultra-low-molecular-weight heparins." *Best Pract Res Clin Haematol* (2004) 17(1): 77-87). Indeed, LMWH have better predictability of the pharmacodynamic effect, an excellent bioavailability after s.c. administration and a lower risk of heparin induced thrombocytopenia (Boneu, B. "Low molecular weight heparins: are they superior to unfractionated heparins to prevent and to treat deep vein thrombosis?" *Thromb Res* (2000) 100(2): V113-20). Gerotziafas, G. T., A. D. Petropoulou, et al. "Effect of the anti-factor Xa and anti-factor IIa activities of low-molecular-weight heparins upon the phases of thrombin generation." *J Thromb Haemost* (2007) 5(5): 955-62). Unfortunately, their parenteral administration is a main disadvantage especially in the long term outpatient therapy.

The development of suitable oral dosage forms would be a major improvement in the administration of said LMWH, since oral administration is the most convenient physiological route. Despite the strong anionic charge and important molecular size of LMWH, researchers have tried for many years to develop oral formulation of these macromolecules (Jaques Lb, "Heparins—Anionic Poly-Electrolyte Drugs" *Pharmacol. Rev.*, (1979) 68).

Heparins are GAG macromolecules composed of a mixture of different chains lengths: their composition is very heterogeneous (Hemker, H. C. and S. Beguin, Eds. (1994). Low-Molecular-Weight Heparins in Prophylaxis and Therapy of Thromboembolic Diseases. Fundamental clinical cardiology Editions Medicales Internationales). Low-Molecular-Weight Heparins in Prophylaxis and Therapy of Thromboembolic Diseases. Fundamental clinical cardiology Editions Medicales Internationales). They act by linking to antithrombin, a natural inhibitor of the coagulation cascade. The capacity of heparin to bind and catalyze the antithrombin (AT) action is selectively supported by a specific pentasacharidic structure, present only in one quarter of the total population chains (Choay, J. "Une nouvelle approche de la chimie de l'héparine et de ses fragments: structure et synthèse." *Angéiologie* (1986) 38(4): 123-132). The heparin-AT complex has an equimolar inhibition action on either the Xa or the IIa factor of the coagulation cascade depending on the length of the chain of heparin which presents the pentasacharidic structure.

Although some of these compounds can be administered orally, they have very low and/or very erratic gastrointestinal absorption, which poses a serious problem for marketing and developing therapeutic regimens for GAG drugs, since the results obtained differ greatly from those expected due to this behaviour in the LADME pharmacokinetic processes (Liberation, Absorption, Distribution, Metabolization and Elimination). Furthermore, these macromolecules have a hydrophilic character and are typically very poorly permeable through gastrointestinal mucosa. Gastrointestinal mucosa easily allows small lipophilic molecules to pass through, but it is very impermeable to charged hydrophilic macromolecules. Furthermore, poor permeability is exacerbated by the fact that the digestive tube is coated with negatively charged mucosa, which has a natural tendency to repel the molecules of the same charge.

Heparins possess anticoagulant activity affected by inactivation of certain coagulation cascade factors. Due to their anticoagulant properties (related with the inhibition of factor IIa) and antithrombotic properties (by the inhibition of factor Xa), heparins are used for the prevention and treatment of thromboembolic diseases (Low- and ultra-low-molecular-weight heparins. *Best Pract Res Clin Haematol*. (2004), 17: 77-87): a) in prevention, to reduce the incidence of thromboembolic complications after prolonged immobilization due to a disease, and after surgical interventions (Prevention of venous thromboembolism. Agnelli and Sonaglia., *Tromb Res*. (2000), 97: V49-62); b) in curing, for the treatment of deep vein thrombosis (*Treatment of venous thromboembolism. Ageno. Tromb Res*. 2000, 97: V63-72.), of pulmonary embolisms, of disseminated intravascular coagulation, acute arterial obstruction and the acute phase of myocardial infarction.

Currently, heparin is extracted from porcine or bovine intestinal mucosa (Heparins: all a nephrologist should know. Hetzel et al. *Nephrol Dial Transplant*. (2005), 20: 2036-42). The unfractionated heparin is a heterogeneous mixture of sulfated mucopolysaccharide chains whose molecular mass is between 3,000 and 30,000 daltons. Its average molecular mass is 15,000 Daltons, and it corresponds to a heparin molecule of around 45 osidic units (Molecular weight dependency of the heparin potentiated inhibition of thrombin and activated factor X. Effect of heparin neutralization in plasma. Andersson et al. *Thromb Res*. (1979), 15: 531-41).

After chemical or enzymatic depolymerisation is performed, heparins consisting of shorter chains, and consequently with a lower molecular mass between 1,000 and 10,000 Daltons, are produced. Their average molecular mass is 4,500 Daltons. These heparins, called low molecular weight heparins (LMWH), are then distinguished from unfractioned heparins (UH) by a predominantly anti-Xa activity.

Heparin acts by the intermediation of a cofactor: antithrombin III (ATIII), which is a natural plasma inhibitor of coagulation (Heparin and Low-Molecular-Weight Heparin: The Seventh ACCP Conference on Antithrombotic and Thrombolytic Therapy. Hirsh and Raschke. Chest. 2004; 126:

188S-203S) and it behaves as a catalyst with respect to ATIII. ATIII has a slow and progressive action. Once the heparin has been fixed to the ATIII by the intermediation of the pentasaccharide fragment, this action becomes immediate. This fixation causes a change in the formation of the ATIII which then permits the irreversible fixation thereof on the active site of serine proteinase-type coagulation factors (factors IIa, Xa and IXa, mainly). Then, heparin is released intact, and can then react with a new antithrombin molecule.

The pharmacodynamic effect of heparins depends on the chain length of oligosaccharides. Indeed, to inhibit the thrombin, heparin should be fixed on ATIII and on thrombin through a pentasaccharide block. On the other hand, to inhibit factor Xa, heparin should only fix to ATIII by the pentasaccharide block. Thus, the fragments with a molecular mass (MM) below 5,400 Da, i.e. 18 saccharide units, lose their capacity to be simultaneously fixed to thrombin and ATIII, and will thus have an essentially anti-Xa activity. The fragments with a MM greater than or equal to 5,400 Da will be both anti-Xa and anti-IIa. Standard heparin comprises fragments with a variable molecular mass of 2,000 to 30,000 Da, and therefore has activity on the two factors, Xa and IIa (Heparin and Low-Molecular-Weight Heparin: The Seventh ACCP Conference on Antithrombotic and Thrombolytic Therapy. Hirsh and Raschke. Chest. 2004; 126: 188S-203S). It therefore has both an antithrombotic and an anticoagulant activity, in comparison with low molecular weight heparins, which are essentially antithrombotic agents with a predominance of anti-Xa activity. Venous thromboembolic disease continues to be responsible for important morbidity and/or mortality. In fact, in the United States, the number of persons hospitalized for this reason is estimated at between 300,000 and 600,000 per year. Furthermore, this disease, due to the pulmonary embolism of which it is the cause, would be responsible for 50,000 (Development of oral heparin therapy for prophylaxis and treatment of deep venous thrombosis. Money and Gorka. *Caridovasc Surg.* (2001), 9: 211-8) to 100,000 deaths per year in the United States (Prevention of venous thromboembolism. Agnelli and Sonaglia. *Tromb Res.* (2000), 97: V49-62).

Since heparin acts on the coagulation factors by a catalysis mechanism mediated by ATIII, the measurement of its plasma concentration does not constitute an efficient means to determine its biological activity. The procedures used should instead reflect heparin's capacity to inhibit factors Xa and IIa. For this reason, different measurement process can be used in human beings and animals: a) the measurement of the coagulation factor activity, expressed in units of inhibition of Xa or IIa activity; b) the measurement of the haemorrhaging time determined by the activated partial thromboplastin time (aPTT) (This test explores the intrinsic route of the coagulation measuring the coagulation time of decalcified and platelet-impoverished plasma in the presence of a platelet equivalent (cephalin) and calcium.); c) the measurement of the prothrombin time exploring the intrinsic coagulation route; this procedure uses recalcified blood plasma in the presence of tissue thromboplastin (Digestive absorption of heparin with alternative formulations. Ubrich et al., 2002. *S.T.P. Pharma Sciences* (2002), 12: 147-55). There is another process which is performed only in animals, and consists of measuring the variation in the size of a thrombus. This does not permit quantification of the response, but it shows whether there is a proven pharmacological action of the anticoagulant.

Heparin is an active compound whose absorption through gastrointestinal mucosa is limited following oral administration, since absorption through the mucosa will not be limited by its solubility but by its low permeability with respect to the intestinal membrane mainly due to its negative charge. Prior to the present invention, the permeability of heparins through the digestive epithelium has been recognized as being very low, which makes the administration of heparin/formulations containing heparin by oral route very difficult. For this reason, the route of administration chosen in the majority of the aforementioned classes of compounds is the route of parenteral administration, mainly via intramuscular or subcutaneous injections. At present, some of these compounds are even administered via nasal and pulmonary formulations as in the case of salmon calcitonin or insulin (Alpar, H. J.; Somavarapu, S.; Atuah, K. N.; Bramwell, V. W. *Adv. Drug Deliv. Rev.* 2005, 57, 411-430; Platz et al. U.S. Pat. No. 6,921,527).

Nevertheless, a problem posed by parenteral administration is that, in most cases, these treatments require long periods of therapy such as, for example, in some types of diabetes, for which treatment is needed for the entire life, the frequency of administration being daily. This is a great disadvantage, mainly for the patient, and for this reason it is important to look for alternative routes. Fundamentally, oral administration, which is the most convenient for the patient and is the most economical, should correspond to the preferred one; however, for oligosaccharides and proteins, designing formulations prepared to be administered orally is problematic and involves many complications, since the gastrointestinal tract degrades these active compounds. This means that they should be formulated to enable, first, the pharmaceutical formulation to pass through the stomach without degrading the active compound and, once it reaches the target mucosa, release a large quantity of the active compound selectively on the mucosa wall in a relatively short time interval, thereby providing the desired therapeutic or preventive activity.

Strategies that have been developed to increase bioabsorption (permeability) of GAG-type macromolecules through the mucosa include:

Design of prodrugs ("Prodrug strategies to enhance the intestinal absorption of peptides". Gangwar et al. *Drug Discovery Today* (1997), 2(4), 148-155.)

Design of salts of the glycosaminoglycan, with a change in the chemical structure of the glycosaminoglycan (PCT International Publication WO2007079252).

Development of absorption promoters (European Patent EP1652836; Iceland Patent 200602146)

Development of mucoadhesive devices such as bioadhesive systems or intestinal patches (Oral delivery of macromolecules using intestinal patches: applications for insulin delivery. *Journal of Controlled Release* (2004), 98(1), 37-45)

Development of particulate systems.

Current research in pharmacology (based on particulate systems) is focused on two different but complementary areas: targeting and controlled release systems. The release profile of the active compound depends on numerous parameters: size, distribution, porosity, degradation, permeability of the polymer, etc. An example of oral multiparticulate dosage form is based on a mixture of a biodegradable polymer and a non-biodegradable polycationic polymer. It has obtained mean absolute bioavailabilities of 59% and 48% with nanoparticles of LMWH (Hoffart, V., A. Lamprecht, et al. "Oral bioavailability of a low molecular weight heparin using a polymeric delivery system." *J Control Release* (2006) 113(1): 38-42) and microparticles of UFH (Jiao, Y., N. Ubrich, et al. "Anticoagulant activity of heparin following oral administration of heparin-loaded microparticles in rabbits." *J Pharm Sci* (2002) 91(3): 760-8), respectively.

U.S. Publication 2005/0020539 A1 discloses pharmaceutical compositions and methods of preparation for the oral administration of heparin for its selective release in the intestine, which comprises a structure of multiple matrices which comprises a) an internal matrix of amphiphilic compounds and lipophilic compounds wherein the active compound is at least partially embedded and b) an outer hydrophilic matrix wherein matrix a) is dispersed. Plural matrices with amphiphilic compounds and lipophilic compounds are required in order to obtain a slow dissolution profile.

For the particles to have the desired activity, homogenous degradation or erosion throughout the polymeric mass is preferred in order to achieve a suitable release. Also, a suitable surface potential is preferred so that the particles approximate the absorption mucosa. Currently the effort of large multinational companies in the pharmaceutical sector is focused on the development of colloidal systems with reduced particle size, as a strategy to increase the systemic bioavailability of active compounds.

Oral administration continues being an attractive route for the release of pharmacologically active molecules. Its easy administration, the absence of pain associated to the administration, the greater acceptance by the patient, and favorable cost/benefit ratio have turned these oral formulations into the most widely used for the administration of active compounds.

One approach for improving the oral absorption is the use of absorption enhancers like sodium N-[8(-2-hydroxybenzoyl)amino]decanoate (SNAD) designed for specific facilitation of LMWH intestinal absorption in similar fashion as sodium N-[8(-2-hydroxybenzoyl)amino]caprylate (SNAC) with UFH. Indeed the bioavailability of an oral administration of UFH together with the delivery agent SNAC in rats was 6% (Leone-Bay, A., D. R. Paton, et al. "Acylated non-alpha-amino acids as novel agents for the oral delivery of heparin sodium, USP." *J Control Release* (1998) 50(1-3): 41-9).

Another approach is based on the synthesis of new heparin derivatives by coupling LMWH with deoxycholic acid (DOCA). After oral administration of LMWH-DOCA in DMSO to mice, the bioavailability was 17.6% (Kim, S. K., B. Vaishali, et al. "Oral delivery of chemical conjugates of heparin and deoxycholic acid in aqueous formulation." *Thromb Res* (2006) 117(4): 419-27).

PCT International Publication WO2007079252 discloses a quaternary ammonium salt of an acid drug in the form of a suspension or an emulsion, suitable for parenteral administration and providing a sustained release of the drug. In one embodiment, the invention is directed to a long term sustained release composition for parenteral administration. In this case the chemical structure of heparin has been modified.

U.S. Pat. No. 4,703,042 discloses orally active salts of polyanionic heparinic acid with selected polycationic materials. The salts are stable lipoidol "ion-pairs" which can be absorbed through the gastrointestinal wall and which slowly release heparinic acid to achieve long-lasting anticoagulant activity.

U.S. Pat. No. 3,482,014 discloses acid salts of heparin (sodium acid heparinate), in contrast to the known neutral salts of heparin, for the preparation of enteric pills or tablets.

Other formulations that might include heparin or related compounds are disclosed in U.S. Publications No. 20010024658, No. 20020160049, No. 20030161884, No. 20030091623, No. 20030198619, No. 20060018933, No. 20060018934, No. 20060024365, No. 20070154559 and No. 20080275001 and U.S. Pat. No. 5,639,469, U.S. Pat. No. 5,849,327, U.S. Pat. No. 5,900,252, U.S. Pat. No. 6,248,363, U.S. Pat. No. 6,458,383, U.S. Pat. No. 6,677,318, U.S. Pat. No. 6,692,771, U.S. Pat. No. 6,919,091, U.S. Pat. No. 7,393,840 and U.S. Pat. No. 7,674,767. U.S. Publ. No. 20060018933 No. 20060018934 and No. 20060024365 all require that the GAG drug be present in excess (100:1 to 100:75 weight ratio). All of the other patents and publications require complex formulations for the dosage forms disclosed therein in order to enhance absorption of the GAG drug.

There is still a need in the art for a pharmaceutical form (composition, dosage form) for the administration, delivery and release of glycosaminoglycans that achieves an efficient and rapid absorption by mucosal route of said glycosaminoglycans after their administration, in particular after oral administration.

BRIEF DESCRIPTION OF THE INVENTION

It has surprisingly been found by the inventors that it is possible to prepare pharmaceutical compositions and dosage forms that provide fast release and improved mucosal absorption of glycosaminoglycans, particularly heparin and heparin-related compounds. In particular, it has been found that, in contrast to some inventions of the prior art where the charges of heparin are completely or nearly completely neutralized by a cationic or polycationic material, when the charges of the glycosaminoglycan, as for instance heparin, are only partially neutralized with selected cations or polycations, so that heparin maintains certain degrees of freedom, both the rapid release and the improved mucosal absorption of the glycosaminoglycanes, for instance via the intestinal mucosa, are performed in a rapid and effective way, are provided. It has also been found that these pharmaceutical compositions and dosage forms are only able to adequately provide these functions as long as the pharmaceutical compositions and dosage forms contain less than 10% w/w of water (moisture), i.e, the water content is 10% wt. or less, wherein the weight ratio of glycosaminoglycan to polycationic compound (polycationic copolymer) ranges from 1:1 to 1:4, the composition consists essentially of about 15 to about 50% wt (or about 20% to about 50%) of glycosaminoglycan, about 85% to about 50% polycationic polymer or copolymer and the composition has a molar excess of sulfate groups over ammonium groups.

One aspect of the invention provides a pharmaceutical composition comprising a glycosaminoglycan and a compound presenting independent or dependent pH quaternary ammonium groups, which is a structure of polymers and copolymers derived from acrylic and methacrylic acids esters, wherein:
  the proportion of ammonium groups in the pharmaceutical composition is between 0.01 to 2.0 μmol ammonium groups/mg pharmaceutical composition,
  the proportion of glycosaminoglycan in the pharmaceutical composition is between 15% to 50% w/w, and
  the pharmaceutical composition comprises a humidity percentage (w/w) lower than 10%.

In some embodiments, the pharmaceutical form comprises a glycosaminoglycan and a compound presenting independent or dependent pH quaternary ammonium groups, which is a structure of polymers and copolymers derived from acrylic and methacrylic acids esters, wherein:
  the proportion of ammonium groups in the pharmaceutical form is between 0.16 to 1.7 μmol ammonium/mg pharmaceutical form,
  the proportion of glycosaminoglycan in the pharmaceutical form is between 20% to 50% w/w, and
  the pharmaceutical form presents a humidity percentage (w/w) lower than 10%.

wherein the charges of the glycosaminoglycan are only partially neutralized with selected cations which are the dependent or independent pH quaternary ammonium groups.

In some embodiments, the pharmaceutical form comprises glycosaminoglycan and a compound presenting independent or dependent pH quaternary ammonium groups, which is a structure of polymers and copolymers derived from acrylic and methacrylic acids esters, wherein:
the proportion of ammonium groups in the pharmaceutical form is between 0.21 to 0.4 μmol ammonium/mg pharmaceutical form,
the proportion of glycosaminoglycan in the pharmaceutical form is between 33% to 50% w/w, and
the pharmaceutical form presents a humidity percentage (w/w) lower than 10%.
wherein the charges of the glycosaminoglycan are only partially neutralized with selected cations which are the dependent or independent pH quaternary ammonium groups.

The charges of the glycosaminoglycan are only partially neutralized with selected cations, which are pH dependent ammonium groups or pH independent quaternary ammonium groups, meaning that less than all of the anionic groups (sulfate groups of the glycosaminoglycan are neutralized by or complexed with the ammonium groups.

The proportion of ammonium groups is generally at or below 2 μmol ammonium groups/mg formulation in order to obtain good results in plasma activity values. The moisture content is generally at or below 10% (w/w) in order to provide improved mucosal absorption, especially absorption via the intestinal mucosa.

In some embodiments, the proportion of ammonium groups in the pharmaceutical composition is about 0.01 to about 2 mmol ammonium groups/mg pharmaceutical composition, about 0.05 to about 1.7 μmol ammonium groups/mg pharmaceutical composition, about 0.16 to about 1.0 μmol ammonium groups/mg pharmaceutical composition, or about 0.21 to about 0.4 μmol ammonium/mg pharmaceutical composition.

In some embodiments, the pharmaceutical composition (form) presents a humidity percentage (moisture content on a w/w basis) lower than 10%, more preferably lower than 8% (w/w) or even more preferably lower than 5% (w/w).

In some embodiments, the pharmaceutical composition comprises a glycosaminoglycan comprising sulfate groups and a polycationic copolymer comprising acrylic and methacrylic acids esters and pH independent primary, secondary or tertiary ammonium groups or pH dependent quaternary ammonium groups, wherein:
the proportion of ammonium groups in the pharmaceutical composition is between 0.16 to 1.7 iμmol ammonium/mg pharmaceutical composition,
the proportion of glycosaminoglycan in the pharmaceutical composition is between 20% to 50% w/w, and
the pharmaceutical composition has a moisture content of 10% wt. or less; and
only a portion (less than all) of the sulfate groups of the glycosaminoglycan are neutralized by the ammonium groups of the polycationic copolymer.

In some embodiments, the proportion of ammonium groups in the pharmaceutical composition is between 0.21 to 0.4 μmol ammonium groups/mg pharmaceutical form, the proportion of glycosaminoglycan in the pharmaceutical composition is between 33% to 50% w/w, and the pharmaceutical composition has a moisture content of 10% wt. or less.

Another aspect of the invention provides a pharmaceutical formulation for the administration of the previously described pharmaceutical composition, said formulation comprising the pharmaceutical composition as defined herein together with pharmaceutical excipients or carriers.

Another aspect of the invention provides a pharmaceutical composition or pharmaceutical formulation as described herein for use as a medicament.

In some embodiments, the invention provides a solid pharmaceutical dosage form comprising a compressed composition consisting essentially of (or consisting of) an admixture of:
15%-50% wt. of polyanionic sulfated glycosaminoglycan comprising anionic sulfate groups; and
85%-50% wt. of polycationic copolymer of acrylic acid ester and methacrylic acid ester comprising cationic ammonium groups; wherein
the compressed composition has a moisture content of about 10% wt. or less; and
the mole ratio of sulfate groups to ammonium groups in the composition is greater than one, whereby less than the total of sulfate groups of the glycosaminoglycan are neutralized by the total of ammonium groups present.

In some embodiments, the dosage form consists essentially of or consists of the compressed composition as defined herein.

In some embodiments, the compressed composition excludes each of or one or more of a biodegradable polymer, additional counterion substance, rate-controlling coating, surfactant, lipid, bile acid, bile acid salt, bile acid ester, fatty acid, fatty acid salt, fatty ester, fatty ether, hyaluronic acid, and hyaluronic acid salt, said exclusion being independently selected upon each occurrence. The compressed composition can exclude plural or all of such components.

In some embodiments, the compressed composition is prepared by direct compression of an admixture of the polycationic copolymer and glycosaminoglycan. In some embodiments, the compressed composition is prepared by agglomeration or granulation of the polycationic copolymer and glycosaminoglycan before compression. In some embodiments, the compressed composition is prepared by pelletization before compression. In some embodiments, the granulation is achieved by mixing the polycationic copolymer and glycosaminoglycan and adding a granulation liquid, then the granule is dried and compressed. In some embodiments, the compressed composition is prepared by adding to the polycationic copolymer a solution containing the glycosaminoglycan, then the granule is compressed. In some embodiments, the granulation is achieved by compaction of the polycationic copolymer and glycosaminoglycan by a roller compaction process, then the agglomerates are compressed. In some embodiments, the compressed composition is a monolithic matrix composition with the glycosaminoglycan dispersed throughout the matrix. In some embodiments, the compressed composition is an uncoated composition.

In some embodiments, the proportion of glycosaminoglycan in the pharmaceutical composition is about 15 to about 50% w/w, about 20 to about 50% w/w, about 25 to about 50% w/w, or about 33 to about 50% w/w based upon the total weight of the composition.

In some embodiments, the proportion of copolymer present in the pharmaceutical composition is about 85 to about 50% w/w, about 80 to about 50% w/w, about 75 to about 50% w/w, or about 67 to about 50% w/w based upon the total weight of the composition. In some embodiments, the weight ratio of GAG to cationic polymer is in the range of about 1:1 to about 1:4.

In some embodiments, less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10% or less than about 5% of the sulfate groups are complexed with or neutralized by the ammonium groups. In some embodiments, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% or at least about 80% of the sulfate groups are complexed with or neutralized by the ammonium groups. The invention includes all embodiments which are combinations of any of the specified minimum and maximum percentages such that the invention includes embodiments wherein at least about 1% and less than about 95%, inclusive of all integer ratios there between, of the sulfate groups are complexed with or neutralized by the ammonium groups.

In some embodiments, the mole ratio of ammonium groups to sulfate groups is in the range of 0.49:0.51 to 0.001:0.999, 0.49:0.51 to 0.01:0.99, 0.49:0.51 to 0.05:0.95, 0.49:0.51 to 0.1:0.9, 0.49:0.51 to 0.15:0.85, 0.49:0.51 to 0.2:0.8, 0.49:0.51 to 0.25:0.75, 0.49:0.51 to 0.3:0.7, 0.49:0.51, 0.45:0.55 to 0.05:0.95, 0.45:0.55 to 0.1:0.9, 0.45:0.55 to 0.15:0.85, 0.45:0.55 to 0.2:0.8, 0.45:0.55 to 0.25:0.75, 0.45:0.55 to 0.3:0.7, 0.45:0.55 to 0.4:0.6, to 0.4:0.6, 0.4:0.6 to 0.05:0.95, 0.4:0.6 to 0.1:0.9, 0.4:0.6 to 0.15:0.85, 0.4:0.6 to 0.2:0.8, 0.4:0.6 to 0.25:0.75, 0.4:0.6 to 0.3:0.7, 0.3:0.7 to 0.05:0.95, 0.3:0.7 to 0.1:0.9, 0.3:0.7 to 0.15:0.85, 0.3:0.7 to 0.2:0.8, 0.3:0.7 to 0.25:0.75, 0.2:0.8 to 0.05:0.95, 0.2:0.8 to 0.1:0.9, 0.2:0.8 to 0.15:0.85 or 0.1:0.9 to 0.05:0.95.

In some embodiments, the glycosaminoglycan is selected from the group consisting of unfractionated heparin, low molecular weight heparin, ultralow molecular weight heparin, chondroitin sulfate, dermatan sulfate, fondaparinux, bemiparin, enoxaparin, tinzaparin, dalteparin, keratan sulfate, parnaparin, reviparin, nadroparin, certoparin, ardeparin and pharmaceutically acceptable salts thereof.

In some embodiments, the ammonium group is a pH dependent primary, secondary or tertiary ammonium group, such as a protonated salt form of a primary, secondary or tertiary ammonium group. In some embodiments, the ammonium group is a pH independent quaternary ammonium group.

In some embodiments, the compressed composition comprises one polycationic copolymer or a mixture of two, three, four or more different polycationic copolymers. In some embodiments, the compressed composition, and dosage form thereof, contain a combination of two different cationic copolymers: a first cationic copolymer comprising quaternary ammonium groups and a second cationic copolymer comprising primary amine, secondary amine or tertiary amine functional groups.

In some embodiments, the polycationic copolymer is a copolymer of acrylic acid ester and methacrylic acid esters comprising protonated primary ammonium groups, protonated secondary ammonium groups, protonated tertiary ammonium groups or quaternary ammonium groups. In some embodiments, the polycationic copolymer is selected from the group consisting of: a copolymer of trimethylammonioethyl methacrylate and ethyl methacrylate or methyl methacrylate; a copolymer of trimethylammonioethyl methacrylate, ethyl acrylate and methyl methacrylate; a copolymer of trimethylammonioethyl methacrylate and ethyl acrylate or methyl acrylate; a copolymer of dimethylaminoethyl methacrylate and ethyl methacrylate or methyl methacrylate; a copolymer of dimethylaminoethyl methacrylate, ethyl acrylate and methyl methacrylate; a copolymer of dimethylaminoethyl methacrylate and ethyl acrylate or methyl acrylate; a copolymer of butyl methacrylate and (2-dimethylaminoethyl)-methacrylate and methyl methacrylate; and a combination thereof. In some embodiments, the cationic copolymer is selected from the group consisting of poly(ethyl acrylate-co-methyl methacrylate-co-trimethylammonioethyl methacrylate chloride) 1:2:0.2, poly(ethyl acrylate-co-methyl methacrylate-co-trimethylammonioethyl methacrylate chloride) 1:2:0.1, poly(butyl methacrylate-co-dimethylaminoethyl methacrylate-co-methyl methacrylate-) 1:2:1, and a combination thereof.

In some embodiments, the moisture content is 10% wt. or less, 9% wt. or less, 8% wt. or less, 7% wt. or less, 6% wt. or less, 5% wt. or less, 4% wt. or less, 3% wt. or less, 2% wt. or less or 1% wt. or less, at least 0.001%, at least 0.01%, at least 0.1%, at least 0.5%, or any combination thereof to provide all ranges including and within the range of 0.001% wt. to 10% wt.

The composition and dosage form of the invention can be adapted for oral, nasal, pulmonary, vaginal or buccal administration so as to deliver GAG drug to the oropharyngeal mucosa, gastrointestinal mucosa, pulmonary mucosa, nasal mucosa, buccal mucosa or vaginal mucosa.

In some embodiments, the compressed composition, and dosage form thereof, provide a Tmax, associated with the plasma Cmax of glycosaminoglycan, in the range of about 1 to about 6 hours after administration to a subject in need thereof. In some embodiments, the compressed composition, and dosage form thereof, provide a plasma Cmax in the range of about 0.15 to about 1 IU of glycosaminoglycan/ml of plasma following administration to a subject in need thereof when a dose of about 20,000 IU to 50,000 IU is administered to a subject in need thereof.

In some embodiments, the invention provides a solid pharmaceutical dosage form comprising (or consisting essentially of or consisting of) a solid monolithic compressed composition consisting essentially of (or consisting of) an admixture of:

15%-50% wt. of polyanionic sulfated glycosaminoglycan comprising anionic sulfate groups present in the range of about 1 to about 5 or about 1.3 to about 4.7 mmoles per g of glycosaminoglycan; and 85%-50% wt. of polycationic copolymer of acrylic acid ester and methacrylic acid ester comprising cationic quaternary ammonium groups present in the range of about 0.3 to about 0.6 μmoles per g of copolymer; wherein the compressed composition has a moisture content of about 10% wt. or less;

the weight ratio of glycosaminoglycan to copolymer is in the range of about 1:1 to about 1:4; and the mole ratio of sulfate groups to ammonium groups in the composition is greater than one, whereby less than the total of sulfate groups of the glycosaminoglycan are neutralized by the total of ammonium groups present.

The invention includes all combinations and subcombinations of the aspects, embodiments and subembodiments described herein.

DETAILED DESCRIPTION OF THE INVENTION

Figure 1:
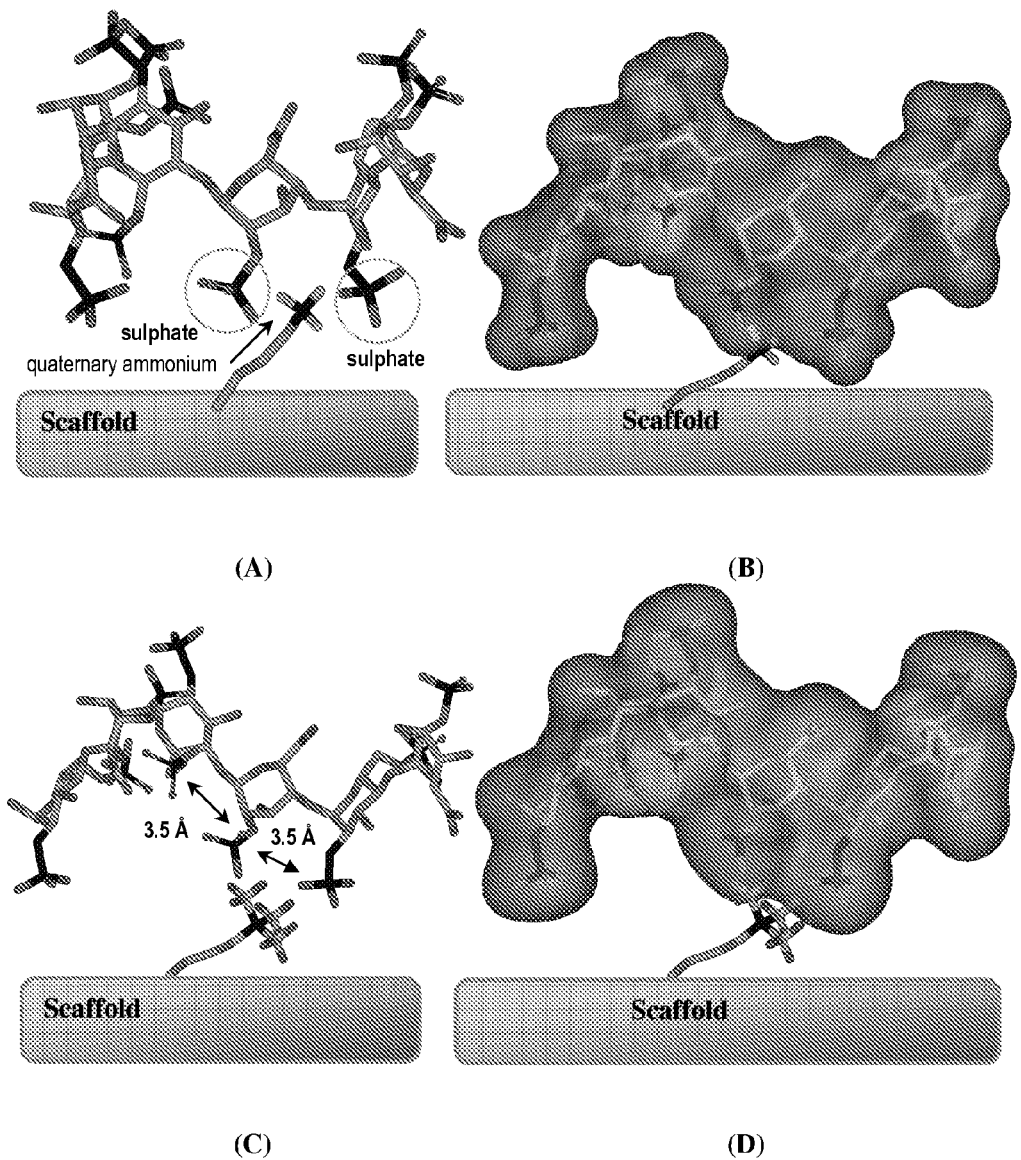
FIG. 1: Provides a schematic view of the three-dimensional partial structure of an ionic complex of heparin and a polycationic polymer depicting the interaction between sulfate groups and ammonium groups. The sulfate groups close to the ammonium are represented circled: (A) The ammonium structure is —NH₃⁺; (C) The ammonium structure is —N(CH₃)₃⁺. (B) and (D) depict the solvent-accessible surface for heparin.

The polycationic compound presenting pH dependent or pH independent ammonium groups can be a compound of formula (I) or (II)

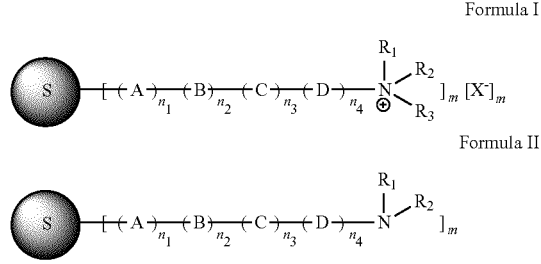

Formula I

Formula II wherein:

is the chemical structure or scaffold to which is attached the chain -(A)-$n_1$-(B)$n_2$-(C)$n_3$-(D)$n_4$- to which is attached the pH dependent or pH independent ammonium groups as part of the global structure;
m is an integer from 1 to 150;
$n_1$, $n_2$, $n_3$ and $n_4$ are independent from each other: 1, 2 or 3;
$R_1$, $R_2$ and $R_3$ are, independent from each other, a radical selected from: H, $CH_3$, $CH_2$—$CH_3$ and $CH_2OH$;
A, B, C and D are, independent from each other, a radical selected from: NH, O, S, HO—P=O, O=P=O, $CH_2$, C=O, CH—OH, CH—$NH_2$; and
[$X^-$] is a pharmaceutically acceptable anion.

In some embodiments, a pharmaceutically acceptable anion [α] in compounds of formula (I) and (II) is, for example, a halide, more particularly, chloride, bromide, fluoride or iodide.

In some embodiments, the polycationic copolymer is a copolymer of acrylic acid ester and methacrylic acid esters comprising primary, secondary, tertiary or quaternary ammonium groups. In some embodiments, the polycationic copolymer is a copolymer of trimethylammonioethyl methacrylate and ethyl methacrylate or methyl methacrylate, a copolymer of trimethylammonioethyl methacrylate, ethyl acrylate and methyl methacrylate (otherwise known as "ammonio methacrylate copolymer Type A" (EUDRAGIT® RL) or "ammonio methacrylate copolymer Type B" (EUDRAGIT® RS)), a copolymer of trimethylammonioethyl methacrylate and ethyl acrylate or methyl acrylate, a copolymer of dimethylaminoethyl methacrylate and ethyl methacrylate or methyl methacrylate, a copolymer of dimethylaminoethyl methacrylate and ethyl acrylate and methyl methacrylate, a copolymer of dimethylaminoethyl methacrylate and ethyl acrylate or methyl acrylate, a copolymer of butyl methacrylate and (2-dimethylaminoethyl)-methacrylate and methyl methacrylate (otherwise known as EUDRAGIT® E)

Particular grades of EUDRAGIT® RL copolymer include the RL PO, RL 100, RL 30D and RL 12.5 grades. Particular grades of EUDRAGIT® RS copolymer include the RS PO, RS 100, RS 30D and RS 12.5 grades. Particular grades of EUDRAGIT® E copolymer include the E 100, E PO and E 12.5 grades.

The generic structure of EUDRAGIT® RS and RL can be represented generally as follows, wherein it contains different amounts of the various monomers:

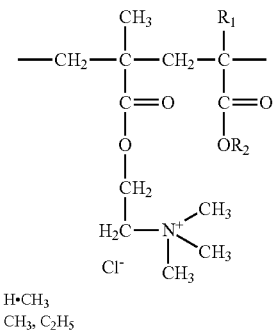

$R_1 = H \cdot CH_3$
$R_2 = CH_3, C_2H_5$

More specifically, the generic substructure of the repeat units of EUDRAGIT® RS and RL can be represented generally as follows, keeping in mind that the three monomers depicted are present in different amounts (see respective proportions below) in the copolymer:

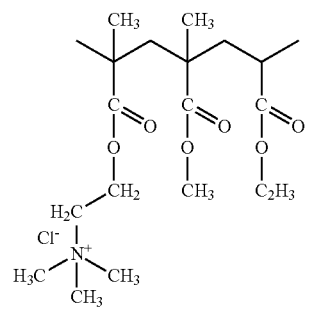

EUDRAGIT® RL (CAS RN: 33434-24-1; IUPAC name: Poly(ethyl acrylate-co-methyl methacrylate-co-trimethylammonioethyl methacrylate chloride) 1:2:0.2 INCI name: Acrylates/Ammonium Methacrylate Copolymer) is more fully described in the monographs of Ph. Eur, (Ammonio Methacrylate Copolymer, Type A), USP NF (Ammonio Methacrylate Copolymer, Type A-NF) and JPF (Aminoalkyl Methacrylate Copolymer RL). It has a weight average molar mass of about 32,000 g/mol, an alkali value of 28.1 mg KOH/g polymer, and glass transition temperature (Tg) of about 70° C. EUDRAGIT RL comprises an average of 0.6±0.05 µmol of ammonium groups per mg of copolymer.

EUDRAGIT RS (CAS RN: 33434-24-1; IUPAC name: Poly(ethyl acrylate-co-methyl methacrylate-co-trimethylammonioethyl methacrylate chloride) 1:2:0.1 INCI name: Acrylates/Ammonium Methacrylate Copolymer) is more fully described in the monographs of Ph. Eur, (Ammonio Methacrylate Copolymer, Type B), USP NF (Ammonio Methacrylate Copolymer, Type B-NF) and JPF (Aminoalkyl Methacrylate Copolymer RS). It has a weight average molar mass of about 32,000 g/mol, an alkali value of 15.2 mg KOH/g polymer, and glass transition temperature (Tg) of about 65° C. EUDRAGIT RS comprises an average of 0.32±0.03 µmol of ammonium groups per mg of copolymer.

The generic substructure of the repeat units of EUDRAGIT E can be represented as follows, keeping in mind that the three monomers depicted are present in different amounts (see respective proportions below) in the copolymer:

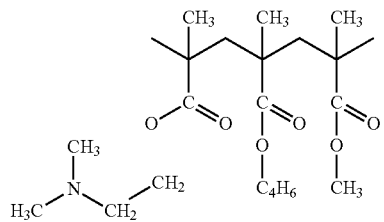

EUDRAGIT E (CAS RN: 24938-16-7; IUPAC name: Poly (butyl methacrylate-co-dimethylaminoethyl methacrylate-co-methyl methacrylate-) 1:2:1 INCI name: Acrylates/Dimethylaminoethyl Methacrylate Copolymer) is more fully described in the monographs of Ph. Eur, (Basic butylated Methacrylate Copolymer), USP NF (Amino Methacrylate Copolymer-NF) and JPF (Aminoalkyl Methacrylate Copolymer E). It has a weight average molar mass of about 47,000 g/mol, an alkali value of 180 mg KOH/g polymer, and glass transition temperature (Tg) of about 48° C. EUDRAGIT E comprises an average of 3.2±0.3 µmol of ammonium groups per mg of copolymer.

In some embodiments, the polycationic copolymer comprises ammonium groups present in the range of about 0.2 to about 3.5 µmol, 0.2 to about 3.2 µmol, about 0.2 to about 0.4 about 0.5 to about 0.7 µmol, about 0.3 to about 3.2 µmol, about 0.3 to about 0.6 µmol, or about 3 to about 4 µmol of ammonium groups per mg of copolymer. In some embodiments, the ammonium groups are quaternary ammonium groups.

Various grades of Eudragit® copolymers are provided by Evonik Röhm GmbH (Darmstadt, Germany, www.evonik.com). EUDRAGIT® RS and RL copolymers have an overall positive charge with a low concentration in quaternary ammonium groups: Eudragit RL 100/RL PO has 8.85-11.96% trimethylammonioethyl methacrylate units on dry substance (DS) and Eudragit RS 100/Eudragit RS PO has 4.48-6.77% trimethylammonioethyl methacrylate units on DS. These copolymers are non-biodegradable synthetic copolymers. Accordingly, in some embodiments, the polycationic copolymer comprises 8.85-11.96% wt. trimethylammonioethyl methacrylate units on a dry substance basis or 4.48-6.77% wt. trimethylammonioethyl methacrylate units on a dry substance basis. Eudragit® E is a cationic copolymer based on dimethylaminoethyl methacrylate and neutral methacrylic esters. Eudragit® E 100, E PO and E 12.5 have 20.8 to 25.5% of dimethylaminoethyl (DMAE) groups on dry substance. Accordingly, in some embodiments, the polycationic copolymer comprises 20.8-25.5% wt. dimethylamionoethyl units on a dry substance basis.

The number of micromoles of ammonium groups per g of copolymer (or per g of composition) can be calculated by: 1) calculating the approximate weight percentage of ammonium groups according to Ph. Eur. 2.2.20 "Potentiometric titration" or USP <541>; b) using the weight percentage value of a) to calculate the micromoles of ammonium groups per g of copolymer or per g of composition. For example:

Step 1: EUDRAGIT RS comprises about 4.48 to about 6.77% or an mean of about 5.62% of ammonio methacrylate monomers per g of composition.

Step 2: micromoles of ammonium groups per g copolymer or per g of composition For 400 mg of EUDRAGIT RS, there are about 22.48 mg of N(CH$_3$)$_3$ groups. The molecular weight of cationic monomer is 172 g/mole; therefore, there are about 0.13 millimoles of N(CH$_3$)$_3$ groups per 400 mg of copolymer, and about 0.325 micromoles of N(CH$_3$)$_3$ groups per mg of EUDRAGIT RS. This means that a composition weighing 603 mg (200 mg of bemiparin, 400 mg of EUGRAGIT, 3 mg of lubricant) contains about 0.215 micromoles of N(CH$_3$)$_3$ groups per mg of composition.

Based upon the above, EUDRAGIT RS has about 0.325 micromoles of ammonium group per mg of copolymer, EUDRAGIT RL has about 0.605 micromoles of ammonium group per mg of copolymer and EUDRAGIT E has about 3.215 micromoles of ammonium group per mg of copolymer.

The number of micromoles of sulfate groups per g of GAG molecule (or per g of composition) can be calculated by: 1) calculating the approximate weight percentage of sulfate groups in a dissacharide unit of the GAG molecule; b) using the weight percentage value of a) to calculate the micromoles of sulfate groups in the GAG molecule.

Step 1: weight percent of sulfate groups per dissacharide unit of heparin $$\text{Wt. \% SO}_3 = (A \times MW(SO_3) \times 100)/MW(\text{dissach.}),$$

wherein A (>1.8) is the approximate number of sulfate groups per dissacharide.

For example, for heparin, LMWH and ULMWH: Wt. % SO$_3$=(2×80×100)/600=26.67%, 600 is an approximation of the average molecular weight of the dissacharide and A is approximately 2.

Step 2: micromoles of sulfate groups per g heparin or per g of composition

For 200 mg of bemiparin, there are about 53.3 mg of SO$_3$ groups. The molecular weight of SO$_3$ is 80 g/mole; therefore, there are about 0.67 millimoles of SO$_3$ groups per 200 mg of bemiparin and about 3.3 micromoles of SO$_3$ groups per mg of bemiparin ((0.67×1000)/200). This means that a composition weighing 603 mg (200 mg of bemiparin, 400 mg of copolymer, 3 mg of lubricant) contains about 1.11 micromoles of SO$_3$ groups per mg of composition ((0.67×1000)/603).

Based upon the above, the theoretical percentage of SO$_3$ groups complexed with or neutralized by N(CH$_3$)$_3$ groups for a composition weighing 603 mg (200 mg of bemiparin, 400 mg of copolymer, 3 mg of lubricant) is about 19.5% and the molar ratio of N(CH$_3$)$_3$ groups to SO$_3$ groups is about 1:5.1.

The table below provides some approximate ranges for the weight ratio of GAG:copolymer and the percentage of sulfate groups neutralized by (complexed with) ammonium groups. The percentage was determined based upon the micromoles of sulfate groups and micromoles of ammonium groups added to a composition. For example, if the composition contains 20 micromoles of sulfate groups and 15 micromoles of ammonium group, then the percentage of sulfate groups neutralized by the ammonium groups is approximately 75% ((15*100)/20).

less than or equal to 4% wt., less than or equal to 2% wt. or less than or equal to 1% wt., based upon the weight of the dosage form. In some embodiments, the dosage form excludes all pharmaceutically acceptable excipients other than the polycationic copolymer. In some embodiments, the compressed composition excludes all pharmaceutically acceptable excipients other than the polycationic copolymer.

In some embodiments, the dosage form consists essentially of (or consists of) at least 90% wt., at least 92% wt., at least 94% wt., at least 96% wt., at least 98% wt, at least 99% wt. of

|  | EUDRAGIT RS | | EUDRAGIT RL | | EUDRAGIT E | |
| --- | --- | --- | --- | --- | --- | --- |
| Compound | Weight Ratio (GAG:Copoly) | % SO$_3$ Groups Neutralized by Ammonium | Weight Ratio (GAG:Copoly) | % SO$_3$ Groups Neutralized by Ammonium | Weight Ratio (GAG:Copoly) | % SO$_3$ Groups Neutralized by Ammonium |
| Unfractionated Heparin (30% SO3) | 1:1-1:4 | 8.6-34.8 (5-55) | 1:1-1:4 | 16.1-80.4 (5-95) | <1:1 | (5-95) |
| Bemiparin (26.7% SO3) | 1:1-1:4 | 9.7-39.4 (5-60) | 1:1-1:4 | 18.1-90.1 (5-95) | <1:1 | (5-95) |
| Enoxaparin (26.7% SO3) | 1:1-1:4 | 9.7-39.4 (5-60) | 1:1-1:4 | 18.1-90.1 (5-95) | <1:1 | (5-95) |
| Dermatan sulfate (17% SO3) | 1:1-1:4 | 15.2-61.9 (10-85) | <1:4 | (5-95) | <0.6:1 | (5-95) |
| Low Molecular Weight Heparin (26.7% SO3) | 1:1-1:4 | 9.7-39.4 (5-60) | 1:1-1:4 | 18.1-90.1 (5-95) | <1:1 | (5-95) |
| Ultra-low Molecular Weight Heparin (26.7% SO$_3$) | 1:1-1:4 | 9.7-39.4 (5-60) | 1:1-1:4 | 18.1-90.1 (5-95) | <1:1 | (5-95) |
| Chondroitin Sulfate (14% SO3) | 1:1-1:4 | 18.5-74.3 (5-90) | <1:3 | (5-95) | <0.5:1 | (5-95) |
| Fondaparinux (37% SO$_3$) | 1:1-1:4 | 7.1-28.2 (5-50) | 1:1-1:4 | 13-65.2 (5-75) | <1.4:1 | (5-95) |

Values enclosed in parentheses denote preferred values. All values are approximate values. The percentage of sulfate groups complexed with ammonium groups might be determined by Infrared spectroscopy or CPMAS NMR.

Without being held bound to a particular mechanism, it is believed that the improved mucosal absorption of GAG following administration of the dosage form is at least partially due to the fact that the ammonium groups are located in a structured scaffold, such as a polycationic polymer. Experimental data obtained for comparator formulations in Example 12 demonstrate the importance of the attachment of the ammonium group to a polymeric scaffold.

In a particular embodiment, the glycosaminoglycan is bemiparin. In another particular embodiment, the glycosaminoglycan is enoxaparin. Other glycosaminoglycans that could be used in the pharmaceutical forms are chondroitin, dermatan sulfate, fondaparinux and pharmaceutically acceptable salts thereof. In some embodiments, the glycosaminoglycan is selected from the group consisting of unfractionated heparin, low molecular weight heparin, ultralow molecular weight heparin, chondroitin, dermatan sulfate, fondaparinux and pharmaceutically acceptable salts thereof.

The dosage form can, but need not, additionally comprise one or more pharmaceutically acceptable excipients such as, for example, plasticizers, glidants, absorption enhancers, humectants, surfactants, colouring matters, dispersants, etc, or carriers.

In some embodiments, the percentage (w/w) of pharmaceutically excipients in the dosage form, other than the polycationic compound/copolymer, is less than or equal to 10% wt., less than or equal to 8% wt., less than or equal to 6% wt., compressed composition, based upon the weight of the dosage form. The remaining balance can be one or more pharmaceutically acceptable excipients. In some embodiments, the dosage form comprises, consists essentially of or consists of the compressed composition.

In some embodiments, compressed composition consists essentially of 5 to 1000 mg of polycationic copolymer and 1 to 200 mg of glycosaminoglycan, wherein the weight of polycationic copolymer is equal to or exceeds the weight of glycosaminoglycan. In some embodiments, the weight ratio of polycationic copolymer is 1 to 4 fold, 1.1 to 10 fold, 1.5 to 10 fold, 2 to 10 fold, 2 to 8 fold or 2 to 5 fold the weight of glycosaminoglycan.

The invention provides embodiments wherein the compressed composition consists essentially of: a) 85-50% wt. polycationic copolymer, 15-50% wt. glycosaminoglycan, 0.01-1% wt. lubricant and has a moisture content of 10% wt or less; b) 85-50% wt. polycationic copolymer, 15-50% wt. glycosaminoglycan, 0.01-1% wt. lubricant, 0.01-1% wt. glidant and has a moisture content of 10% wt or less; or c) 85-50% wt. polycationic copolymer, 15-50% wt. glycosaminoglycan, 0.01-1% wt. lubricant, 0.01-5% wt. dispersant and has a moisture content of 10% wt or less.

In some embodiments, the compressed composition consists essentially of the following ingredients, wherein the compressed composition has a moisture content of 10% wt. or less, the total balance of ingredients and moisture totals 100% wt., and the weight of copolymer exceeds the weight of glycosaminoglycan:

| Ingredient | I | II | III | IV | V |
|---|---|---|---|---|---|
| GAG | 15-50% | 28-33% | 45-50% | 20-25% | 15-25% |
| copolymer | 85-50% | 62-67% | 45-50% | 75-80% | 75-85% |

In each of the embodiments, the compressed composition, optionally and independently upon each occurrence, further contains 0.1-1% wt. glidant, 0.1-1% wt. glidant, 1-5% wt. dispersant, or a combination thereof.

In some embodiments, the compressed composition consists essentially of (or consists of):
15%-50% wt. of polyanionic sulfated glycosaminoglycan comprising anionic sulfate groups; and
85%-50% wt. of polycationic copolymer of acrylic acid ester and methacrylic acid ester comprising cationic ammonium groups; wherein
the compressed admixture has a moisture content of less than or about 10% wt.; and
the mole ratio of sulfate groups to ammonium groups in the composition is greater than one, whereby less than the total of sulfate groups of the glycosaminoglycan are neutralized by the total of ammonium groups present.

The pharmaceutical composition according to the present invention may be subsequently processed to obtain a pharmaceutical dosage form which is the final product to be administered to a patient. The features of the pharmaceutical dosage form depend on the route of administration, particular release profiles, or other intended effects.

In some embodiments, the dosage form and compressed composition of the invention are adapted for oral administration. The dosage form of the invention is in solid form. In particular, the formulation can be a pellet, granule, tablet or mini-tablet. For example, granules and pellets can be produced and they can also be adapted for the preparation of tablets and/or capsules (Characterization of 5-Fluorouracil Release from Hydroxypropylmethylcellulose Compression-Coated Tablets. Wu et al. *Pharmaceutical Development and Technology* (2007), 12(2), 203-210), or they can be subject to additional treatments such as polymeric coatings of granules produced to provide:

Gastro-resistance: (In vitro dissolution studies of sodium diclofenac coated granules with eudragit L-30D-55 by fluidized-bed system, Silva et al. *Drug Development and Industrial Pharmacy* (2006), 32(6), 661-667), such as, for example, polyvinyl acetate phthalate, hydroxypropyl methylcellulose phthalate, acrylic copolymers as methacrylic acid and methacrylic ester copolymers, hydroxypropylmethylcellulose acetate succinate, etc., Mucoadhesiveness: such as, for example, chitosan.

The compressed composition and dosage form can be adapted to complete release of glycosaminoglycan in 24 hours or less, 12 hours or less, 11 hours or less, 10 hours or less, 9 hours or less, 8 hours or less, 7 hours or less, 6 hours or less, 5 hours or less, 4 hours or less, 3 hours or less, 2 hours or less or 1 hour or less following administration or placement in an aqueous environment. The compressed composition and dosage form can be adapted to initiate release of glycosaminoglycan within one hour, within 45 min, within 30 min, within 20 min, within 15 min, within 10 min, within 5 min, within one min, within 30 sec or immediately after administration or placement in an aqueous environment. In some embodiments, the composition and dosage form is adapted to:

a) initiate release immediately after administration and to complete release in 12 hours or less after administration; b) initiate release within one minute after administration and to complete release in 12 hours or less after administration; c) initiate release within 10 minutes after administration and to complete release in 12 hours or less after administration; d) initiate release within 30 min after administration and to complete release in 12 hours or less after administration; e) initiate release within one hour after administration and to complete release in 12 hours or less after administration; f) initiate release within one minute after administration and to complete release in 8 hours or less after administration; g) initiate release within 10 minutes after administration and to complete release in 8 hours or less after administration; h) initiate release within 30 min after administration and to complete release in 8 hours or less after administration; i) initiate release within one hour after administration and to complete release in 8 hours or less after administration; j) initiate release within one minute after administration and to complete release in 6 hours or less after administration; k) initiate release within 10 minutes after administration and to complete release in 6 hours or less after administration; l) initiate release within 30 min after administration and to complete release in 6 hours or less after administration; or m) initiate release within one hour after administration and to complete release in 6 hours or less after administration. In some embodiments, the composition and dosage form of the invention provides an extended release (sustained, continuous or controlled release) of drug through the period of release. The invention includes any combination of these embodiments and subembodiments and therefore includes all integer ranges combining these values.

Various different formulations of compressed compositions according to the invention are detailed in Examples 1-3, 4, 6, 9-12, and 15-20 and comparator formulations are detailed in Examples 5, 7, 8, 12 and 14.

The effect that moisture content of the composition has upon bioabsorption of a glycosaminoglycan is revealed by comparison of the performance of the formulations in Examples 13 and 14 to other formulations described herein. Example 13 details a formulation containing equivalent amounts of EUDRAGIT RS and bemiparin, just as do the formulations of Examples 3 and 10. However, the formulation of Example 13 is a dispersion in water; whereas the formulations of Examples 3 and 10 contain 3.89% wt. and 2.56% wt., respectively, of water. When administered to animals, the formulation of Example 13 did not provide acceptable plasma levels of bemiparin due to poor bioabsorption thereof. The formulation of Example 14 contains a molar ratio of bemiparin to EUDRAGIT RS of 1:2, just as do the formulations of Examples 1, 2, 6, 7, 8, 9 and 19; however, the formulation of Example 14 has a moisture content of 12.07% wt.; whereas, the formulations of Examples 1, 2, 6, 9 and 19 have water contents of 5.79%, 4.67%, 3.92%, 3.44% and 4.03% wt. When administered to animals, the formulation of Example 14 did not provide acceptable plasma levels of bemiparin due to poor bioabsorption thereof. The formulations of Examples 1 to 4 and 9 to 11 have corresponding humidity contents values in range of 2.56-7.85% wt. and elicit substantial GAG mucosal absorption with plasma levels over 0.15 IU/ml. Accordingly, the compressed composition and dosage form of the invention is made to have a moisture content of 10% wt. or less.

The effect that the weight ratio of GAG to polycationic copolymer has upon bioabsorption of the GAG after administration is revealed by comparison of the formulation in Example 5 to the formulations of Examples 1-4, 9-11 and 19.

The respective weight ratios and corresponding Cmax and Tmax values for bemiparin are summarized below.

| Example | Weight Ratio (GAG:Copolymer) | Cmax (IU/ml) | Tmax (hr) |
|---|---|---|---|
| 1 | 1:2 | 0.3 | 4 |
| 2 | 1:2 | 0.33 | 2.5 |
| 3 | 1:1 | 0.23 | 1 |
| 4 | 1:4 | 0.17 | 4 |
| 5 | 1:5 | <0.1 | ND |
| 9 | 1:2 | 0.35 | 2.25 |
| 10 | 1:1 | 0.5 | 2 |
| 11 | 1:4 | 0.2 | 2 |
| 19 | 1:2 | 0.2 | 4 |

ND denotes "not determined".

The data demonstrate that, with the specific copolymers and GAG tested, a weight ratio of GAG to cationic copolymer of 1:5 is too high to provide acceptable bioabsorption and that a weight ratio of 1:1 provides reduced bioabsorption as compared to a weight ratio of 1:2 or 1:3. Accordingly, the invention provides a compressed composition (and dosage form containing the same), wherein the weight ratio of GAG to cationic polymer is in the range of 1:1 to 1:4.

The effect that the chemical structure of the cationic compound has upon the bioabsorption of GAG after administration is revealed by comparison of the formulations in Example 12. Formulations 12B, 12C and 12D, which are not made according to the invention, include lysine, arginine and albumin as the "cationic" compounds. Formulation 12A includes EUDRAGIT RS as the cationic compound. The bioabsorption data obtained for these formulations demonstrate that a polycationic copolymer outperforms the cationic amino acids and protein. Accordingly, the compressed composition, and dosage form thereof, of the invention contains a polycationic copolymer.

The effect that the type of copolymer has upon the bioabsorption of GAG after administration is revealed by comparison of the formulations in Examples 1, 6, 7, 8 and 20. The respective copolymer identities, ionic functional groups, weight ratio of GAG to copolymer, and corresponding Cmax values for bemiparin are summarized below.

| Example | Copolymer | Functional Group | Weight Ratio (bemiparin: copolymer) | Cmax (IU/ml) |
|---|---|---|---|---|
| 1 | EUDRAGIT RS | Trimethyl-ammonium | 1:2 | 0.3 |
| 6 | EUDRAGIT RL | Trimethyl-ammonium | 1:2 | 0.35 |
| 7 | EUDRAGIT E | Dimethyl-amino | 1:2 | 0.05 |
| 8 | EUDRAGIT L | Carboxylate | 1:2 | 0.1 |
| 20 | EUDRAGIT RS + EUDRAGIT E (1:2.56) | Trimethyl-ammonium and dimethyl-amino | 1:2.85 | 0.14 |

The data demonstrate that compositions excluding the cationic copolymer having a quaternary ammonium group do not perform well, since they provide unacceptable plasma levels of bemiparin (Examples 7 and 8). Importantly, the poor performance of the cationic copolymer having a dimethylamino functional group can be improved by including in the same formulation a cationic copolymer having a quaternary ammonium functional group, e.g. trimethylammonium. Accordingly, some embodiments of the compressed composition, and dosage form thereof, contain a cationic copolymer comprising quaternary ammonium groups. Other embodiments of the compressed composition, and dosage form thereof, contain a combination of two different a cationic copolymers: a first cationic copolymer comprising quaternary ammonium groups and a second cationic copolymer comprising primary amine, secondary amine or tertiary amine functional groups.

The data included herein demonstrate that the compressed composition, and dosage forms thereof, can provide an acceptable peak plasma level (Cmax) for glycosaminoglycan following administration thereof. Unacceptable peak plasma levels are below 0.1 IU of glycosaminoglycan/ml of plasma. In some embodiments, the invention provides a Cmax within the range of about 0.13 to about 1, about 0.14 to about 1, about 0.15 to about 1, about 0.17 to about 0.8, about 0.2 to about 1, 0.2 to about 0.8, about 0.2 to about 0.7, about 0.2 to about 0.6, or about 0.2 to 0.4 IU of glycosaminoglycan/ml of plasma when a dose of about 20,000 IU to 50,000 IU is administered to a subject in need thereof. It should be understood that these values might vary depending upon the species of the subject to which the composition or dosage form is administered.

The data included herein demonstrate that the compressed composition, and dosage forms thereof, can provide an acceptable Tmax value for glycosaminoglycan following oral administration thereof. In some embodiments, the Tmax ranges from about 1 to about 6, about 1 to about 5, about 1 to about 4, about 2 to about 5 or about 2 to about 4, about 0.5 to about 6, about 0.5 to about 5, about 0.5 to about 4, about 1 to about 3 or about 1 to about 2 hours after administration thereof.

In some embodiments, at least a portion of the compound presenting ammonium groups, e.g. the polycationic copolymer, forms part of or is disposed at the surface of the compressed composition or dosage form. It has been found that the presence of ammonium charges on the surface improves mucosal absorption of GAG following oral administration.

The invention also provides use of the compressed composition or the dosage form as a medicament One aspect of the invention provides a method of treating a disease or disorder that is therapeutically responsive to glycosaminoglycan comprising: administering to a subject in need thereof a dosage form or compressed composition, as described herein, to provide a therapeutically effective amount of glycosaminoglycan according to a prescribed dosing regimen.

The dosing regimens and doses for the glycosaminoglycans disclosed herein are well known. The dosage form or compressed composition of the invention can be administered according to such dosing regimens and dosages. The glycosaminoglycan can be administered at doses and according to dosing regimens that are clinician-recognized as being therapeutically effective, clinically beneficial, such as doses and dosing regimens as suggested or described by the Food and Drug Administration, World Health Organization, European Medicines Agency (EMA), Therapeutic Goods Administration (TGA, Australia), Pan American Health Organization (PAHO), Medicines and Medical Devices Safety Authority (Medsafe, New Zealand) or the various Ministries of Health worldwide.

Heparin and tinzaparin can be administered to a subject in doses containing about 200, about 400, about 500, about 800, about 1000, about 1500, about 2000, about 3000, about 5000, about 10000, about 15000, about 20000 IU or higher, or combinations thereof. Dalteparin can be administered to a subject in doses containing about 2500, about 5000, about 7500, about 10000, about 125000, about 15000, about 18000, about 20000, about 25000 IU or higher or combinations thereof. Enoxaparin can be administered to a subject in doses containing about 10 mg, about 20, mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg or higher. Fondaparinux can be administered to a subject in doses containing about 1.25 mg, about 2.5 mg, about 3.75 mg, about 5 mg, about 7.5 mg, about 10 mg or combinations thereof. Doses can be administered once, twice, three or more times daily or according to any clinically prescribed dosing regimen.

Since the instant compressed composition and dosage form provide improved bioabsorption of the glycosaminoglycan, it is contemplated that they can be administered less frequently than other dosage forms and/or can be modified to contain less glycosaminoglycan (a lower dose) than other dosage forms, e.g. up to 5% less, up to 10% less, up to 15% less, up to 20% less, up to 25% less, up to 30% less, up to 40% less or even up to 50% less. The glycosaminoglycan can be administered at doses and according to dosing regimens that are less than those currently clinician-recognized as being therapeutically effective, i.e. at doses that are clinician-recognized as being sub-therapeutically effective.

The exemplary formulations disclosed herein have been prepared by a direct compression process, wherein an admixture of glycosaminoglycan and cationic copolymer is formed. The admixture optionally comprises lubricant, glidant, dispersant or a combination thereof. If such other compounds are included in the admixture, they too are mixed with the glycosaminoglycan and cationic copolymer. The admixture is the compressed into a solid monolithic matrix or compressed composition. The admixture or compressed composition can be dried using conventional means known in the pharmaceutical industry to reduce the moisture content thereof to 10% wt. or less or as otherwise specified herein. Alternatively or in addition, one or more or all of the individual ingredients can be further dried before being included in the admixture.

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps.

The phrase "pharmaceutically acceptable" is used herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

One or more of the components can be present in its free base or pharmaceutically or analytically acceptable salt form. As used herein, "pharmaceutically or analytically acceptable salt" refers to a compound that has been modified by complexing it with another compound as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences*, $17^{th}$. ed., Mack Publishing Company, Easton, Pa., 1985, p. 1418, the relevant disclosure of which is hereby incorporated by reference. Pharmaceutically acceptable salts of the glycosaminoglycan can include metal salts such as alkali metal salts, alkaline earth metal salts or transition metal salts. Exemplary salts include sodium, potassium, lithium, calcium, magnesium, zinc, manganese and other non-toxic metal salts.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Example 1

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
|---|---|
| Eudragit ® RS PO | 400 |
| Bemiparin | 200 |
| Mg Stearate | 3 |

This Eudragit® RSPO proportion give rise to a range of 0.173-0.261 (approximately mean of 0.21) µmol ammonium units per milligram of formulation. Ammonium unit was considered as the ammonium methacrylate monomer present on Eudragit® RSPO and not as its hydrochloride salt.

Moisture content of the present tablet composition was determined by weight loss on drying at 100° C. during 15 min. The mean value of humidity was 5.79, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 2:
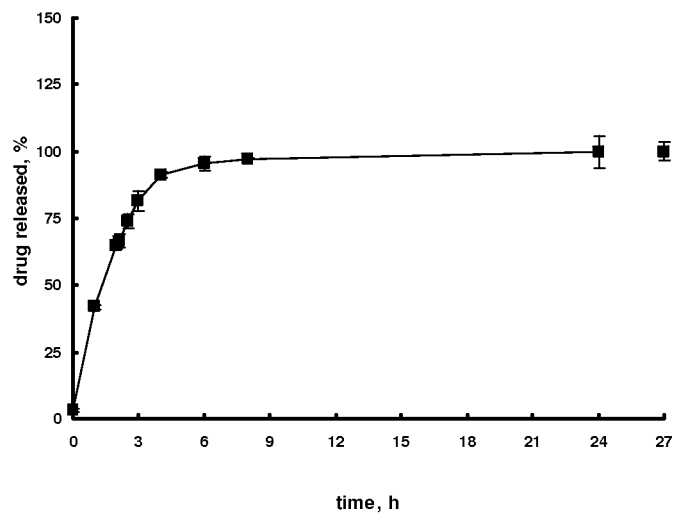
FIG. 2: Bemiparin release profile from tablets prepared according to Example 1 (compound presenting quaternary ammonium groups (Eudragit® RS PO)/glycosaminoglycan (Bemiparin)=400 mg/200 mg) Results are expressed as weight percent of bemiparin released from tablets as a function of time.

Bemiparin release profile from tablets obtained in this example is shown in FIG. 2. Results are expressed as % Bemiparin released from tablets as function of time.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 3:
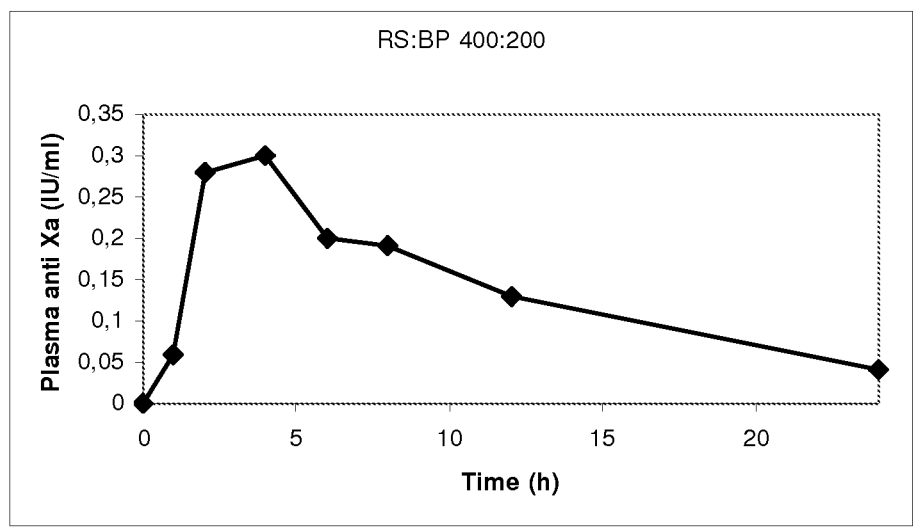
FIG. 3: Plasma anti Xa activity in Beagle dogs after oral administration of 20,000 IU Bemiparin tablets prepared according to Example 1.

Oral administration of 20000 IU Bemiparin in tablets to Beagle dogs resulted in detectable plasma levels as shown in FIG. 3 (Cmax ~0.3 IU/ml; Tmax ~4 hr). This Eudragit® RSPO proportion give rise to a approximately 0.21 µmol ammonium units per milligram of formulation.

Example 2

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
|---|---|
| Eudragit ® RS PO | 200 |
| Bemiparin | 100 |
| Mg Stearate | 1.5 |

This Eudragit® RSPO proportion gives rise to a range of 0.173-0.261 (approximately mean of 0.21) µmol ammonium units per milligram of formulation. Ammonium unit was considered as the ammonium methacrylate monomer present on Eudragit® RSPO and not as its hydrochloride salt.

Humidity content of the tablet corresponding to this example composition was determined by weight loss on drying at 100° C. during 15 min. The mean value of humidity or moisture was 4.67, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 4:
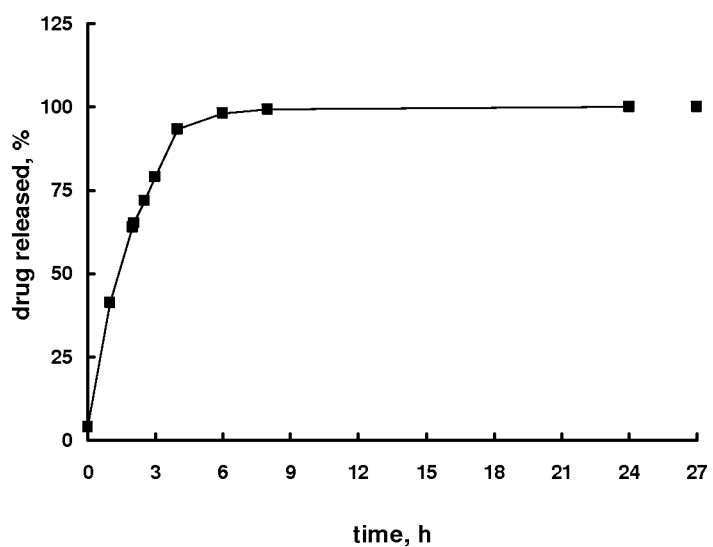
FIG. 4: Bemiparin release profile from tablets prepared according to Example 2 (compound presenting quaternary ammonium groups (Eudragit® RS PO)/glycosaminoglycan (Bemiparin)=200 mg/100 mg). Results are expressed as weight percent of bemiparin released from tablets as a function of time.

Bemiparin release profile from tablets obtained in this example is shown in FIG. 4. Results are expressed as % Bemiparin released from tablets as function of time.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to two tablets per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 5:
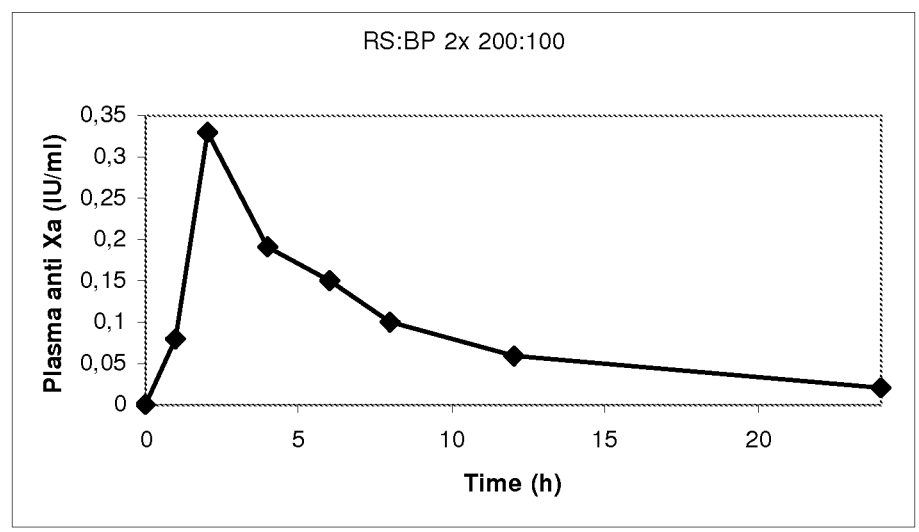
FIG. 5: Plasma anti Xa activity in Beagle dogs after oral administration of 20,000 IU Bemiparin in two tablets of 10,000 IU each prepared according to Example 2.

Oral administration of 20000 IU Bemiparin in tablets to Beagle dogs resulted in detectable plasma levels as shown in FIG. 5 (Cmax ~0.33 IU/ml; Tmax ~2.5 hr). This Eudragit® RSPO proportion gives rise to a approximately 0.21 µmol ammonium units per milligram of formulation.

Example 3

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
|---|---|
| Eudragit ® RS PO | 200 |
| Bemiparin | 200 |
| Mg Stearate | 2 |

This Eudragit® RSPO proportion gives rise to a range of 0.130-0.196 (approximately mean of 0.16) µmol ammonium units per milligram of formulation. Ammonium unit was considered as the ammonium methacrylate monomer present on Eudragit® RSPO and not as its hydrochloride salt.

Humidity or moisture content of the present tablet composition was determined by weight loss on drying at 100° C. during 15 min. The mean value of humidity was 3.89, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 6:
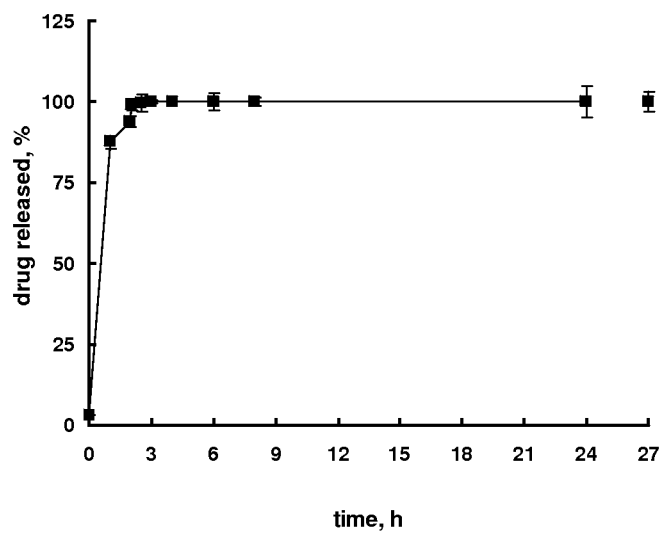
FIG. 6: Bemiparin release profile from tablets prepared according to Example 3 (compound presenting quaternary ammonium groups (Eudragit® RS PO)/glycosaminoglycan (Bemiparin)=200 mg/200 mg). Results are expressed as weight percent of bemiparin released from tablets as a function of time.

Bemiparin release profile from tablets obtained in this example is shown in FIG. 6. Results are expressed as % Bemiparin released from tablets as function of time.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 7:
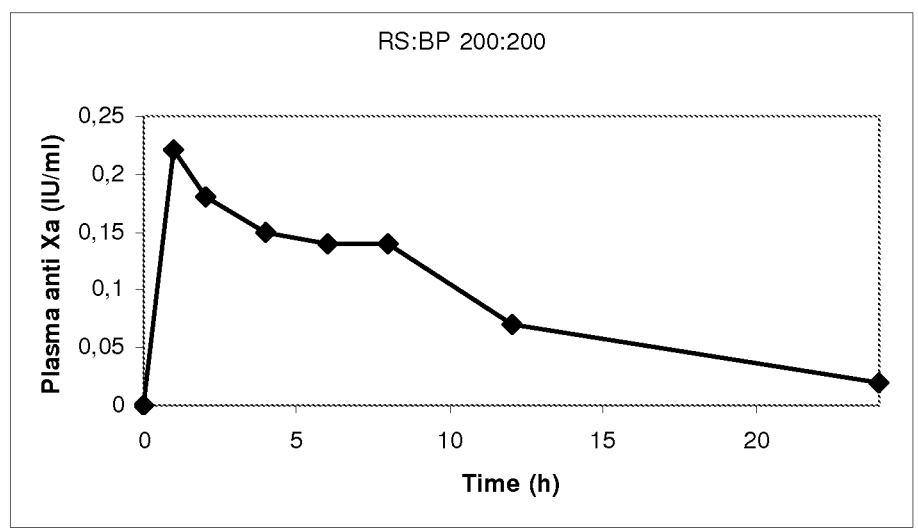
FIG. 7: Plasma anti Xa activity in Beagle dogs after oral administration of 20,000 IU Bemiparin tablets prepared according to Example 3.

Oral administration of 20000 IU Bemiparin in tablets to Beagle dogs resulted in detectable plasma levels as shown in FIG. 7 (Cmax ~0.23 IU/ml; Tmax ~1 hr). This Eudragit® RSPO proportion gives rise to a approximately 0.16 mol ammonium units per milligram of formulation.

Example 4

Bemiparin Tablets

Bemiparin tablets were obtained by direct compression of ingredients in powder by using a single punch tablet press. Composition of the powder mixture, per tablet, was the following:

| Ingredient | Amount (mg) |
| --- | --- |
| Eudragit ® RS PO | 800 |
| Bemiparin | 200 |
| Mg Stearate | 5 |

This Eudragit® RSPO proportion gives rise to a range of 0.207-0.313 (approximately mean of 0.26) μmol ammonium units per milligram of formulation. Ammonium unit was considered as the ammonium methacrylate monomer present on Eudragit® RSPO and not as its hydrochloride salt.

Humidity content of the tablet corresponding to this example composition was determined by weight loss on drying at 100° C. during 15 min. The mean value of humidity was 7.85, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 8:
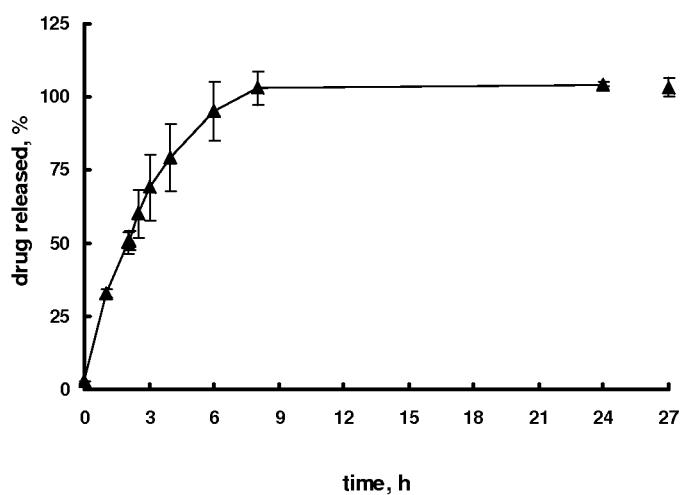
FIG. 8: Bemiparin release profile from tablets prepared according to Example 4 (compound presenting quaternary ammonium groups (Eudragit® RS PO)/glycosaminoglycan (Bemiparin)=800 mg/200 mg). Results are expressed as weight percent of bemiparin released from tablets as a function of time.

Bemiparin release profile from tablets obtained in this example is shown in FIG. 8. Results are expressed as % Bemiparin released from tablets as function of time.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 9:
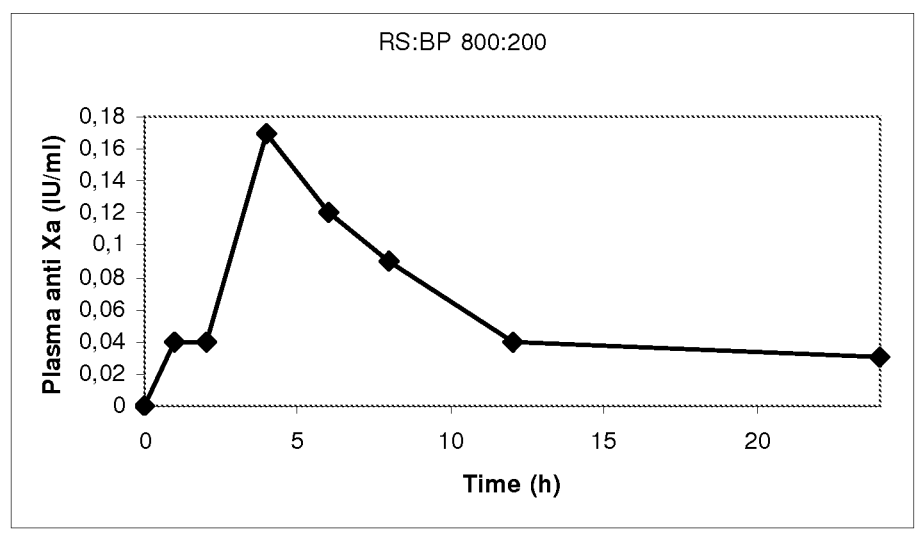
FIG. 9: Plasma anti Xa activity in Beagle dogs after oral administration of 20,000 IU Bemiparin tablets prepared according to Example 4.

Oral administration of 20000 IU Bemiparin in tablets to Beagle dogs resulted in detectable plasma levels as shown in FIG. 9 (Cmax ~0.17 IU/ml; Tmax ~4 hr). This Eudragit® RSPO proportion gives rise to a approximately 0.26 μmol ammonium units per milligram of formulation.

Example 5

Bemiparin Tablets

Bemiparin tablets were obtained by direct compression of ingredients in powder by using a single punch tablet press. Composition of the powder mixture, per tablet, was the following:

| Ingredient | Amount (mg) |
| --- | --- |
| Eudragit ® RSPO | 1000 |
| Bemiparin | 200 |
| Mg Stearate | 6 |

This Eudragit® RSPO proportion gives rise to a range of 0.216-0.326 (approximately mean of 0.27) μmol ammonium units per milligram of formulation. Ammonium unit was considered as the ammonium methacrylate monomer present on Eudragit® RSPO and not as its hydrochloride salt.

Humidity content of the present tablet composition was determined by weight loss on drying at 100° C. during 15 min. The mean value of humidity was 7.15, expressed as (w/w, %).

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Oral administration of 20000 IU Bemiparin in tablets to Beagle dogs did result in plasma levels below to 0.1 IU/ml at all sampling points. This Eudragit® RSPO proportion gives rise to a approximately 0.27 μmol ammonium units per milligram of formulation.

As we can see in example 1 to 5, different GAG to polymer ratios have been tested in order to elucidated which proportion provides better mucosal absorption. 1:5 ratio (see example 5) results in a poor absorption of the compound with a plasma levels below to 0.1 IU/ml at all sampling points. However, 1:1 and 1:2 ratios (see examples 1 to 3) results in a good mucosal absorption, with a plasma levels over 0.20 UI/ml and over 0.1 IU/ml for ratio 1:4 (example 4).

Example 6

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
| --- | --- |
| Eudragit ® RL | 400 |
| Bemiparin | 200 |
| Mg Stearate | 3 |

This Eudragit® RLPO proportion give rise to a range 0.341-0.461 (approximately mean of 0.40) μmol ammonium units per milligram of formulation. Ammonium unit was considered as the ammonium methacrylate monomer present on Eudragit® RLPO and not as its hydrochloride salt.

Humidity content of the tablet corresponding to this example composition was determined by weight loss on drying at 100° C. during 15 min. The mean value of humidity was 3.92, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 10:
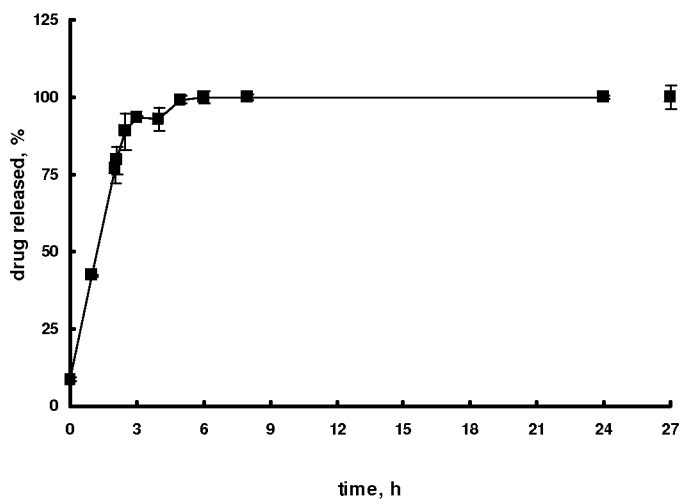
FIG. 10: Bemiparin release profile from tablets prepared according to Example 6 (compound presenting quaternary ammonium groups (Eudragit® RL)/glycosaminoglycan (Bemiparin)=400 mg/200 mg). Results are expressed as weight percent of bemiparin released from tablets as a function of time.

Bemiparin release profile from tablets obtained in this example is shown in FIG. 10. Results are expressed as % Bemiparin released from tablets as function of time. This Eudragit® RSPO proportion give rise to a approximately 0.4 µmol ammonium units per milligram of formulation.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 11:
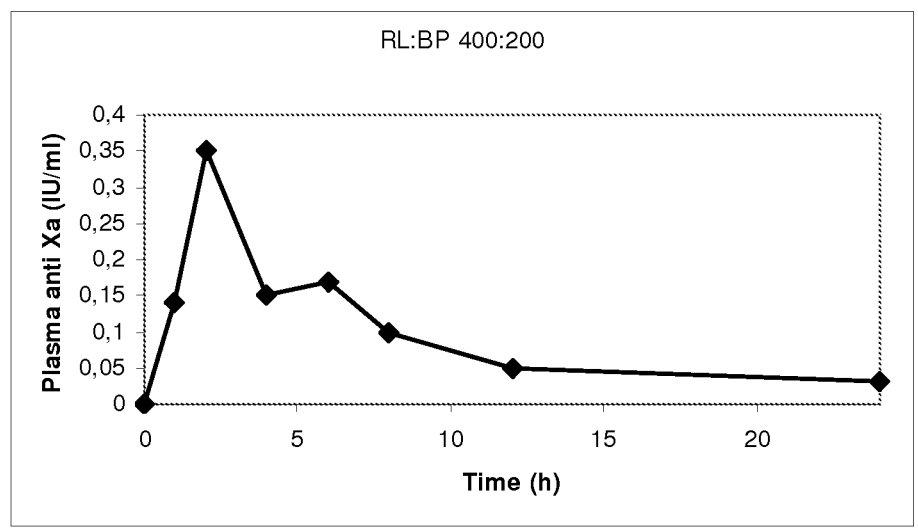
FIG. 11: Plasma anti Xa activity in Beagle dogs after oral administration of 20,000 IU Bemiparin tablets prepared according to Example 6.

Oral administration of 20000 IU Bemiparin in tablets to Beagle dogs resulted in detectable plasma levels as shown in FIG. 11 (Cmax ~0.35 IU/ml; Tmax ~2 hr). This Eudragit® RL proportion gives rise to a approximately 0.4 µmol ammonium units per milligram of formulation.

Comparative Example 7

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
| --- | --- |
| Eudragit ® E | 400 |
| Bemiparin | 200 |
| Mg Stearate | 3 |

This Eudragit® E proportion gives rise to an approximately mean of 2.12 µmol ammonium units per milligram of formulation. Ammonium unit was considered as the dimethyl amino-ethyl group present on Eudragit® E polymer.

Humidity content of the present tablet composition was determined by weight loss on drying at 100° C. during 15 min. The mean value of humidity was 6.19, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 12:
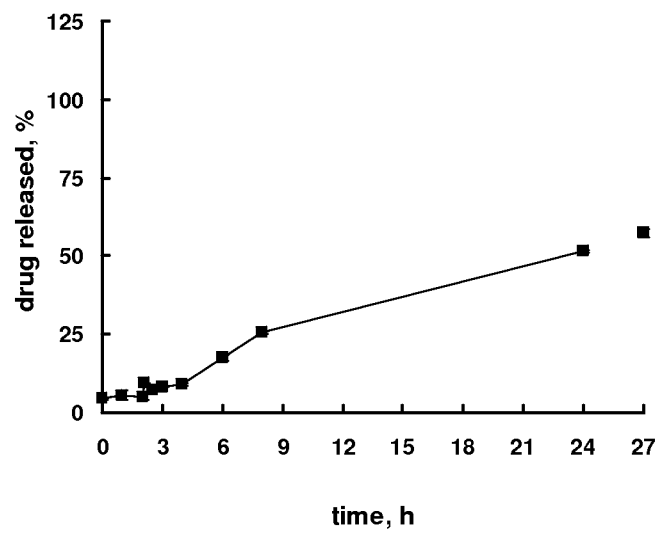
FIG. 12: Bemiparin release profile from tablets prepared according to Example 7 (compound presenting quaternary ammonium groups (Eudragit® E)/glycosaminoglycan (Bemiparin)=400 mg/200 mg). Results are expressed as weight percent of bemiparin released from tablets as a function of time.

Bemiparin release profile from tablets obtained in this example is shown in FIG. 12. Results are expressed as % Bemiparin released from tablets as function of time.

As can be seen in the figure, Eudragit® E strongly complexes Bemiparin and release in 24 h is about 50%. Even if tablet is mechanically disintegrated (point 27 h) no more than 60% of the total Bemiparin becomes dissolved in the release medium.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 13:
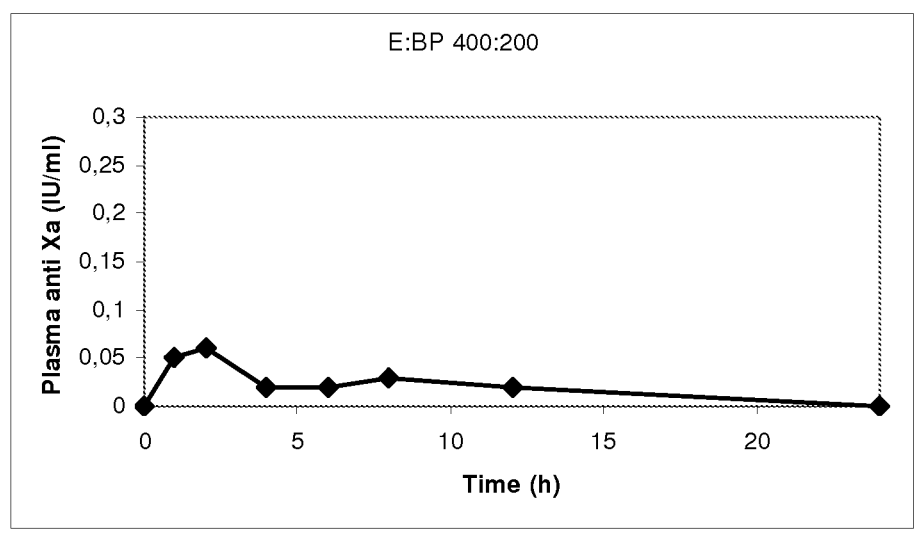
FIG. 13: Plasma anti Xa activity in Beagle dogs after oral administration of 20,000 IU Bemiparin tablets prepared according to Example 7.

Oral administration of 20000 IU Bemiparin in tablets to Beagle dogs resulted in detectable plasma levels as shown in FIG. 13. This Eudragit® E proportion gives rise to a approximately 2.1 µmol ammonium units per milligram of formulation.

Comparative Example 8

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
| --- | --- |
| Eudragit ® L | 400 |
| Bemiparin | 200 |
| Mg Stearate | 3 |

Composition presented in this example has no component providing ammonium groups.

Humidity content of the tablet corresponding to this example composition was determined by weight loss on drying at 100° C. during 15 min. The mean value of humidity was 4.26, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 14:
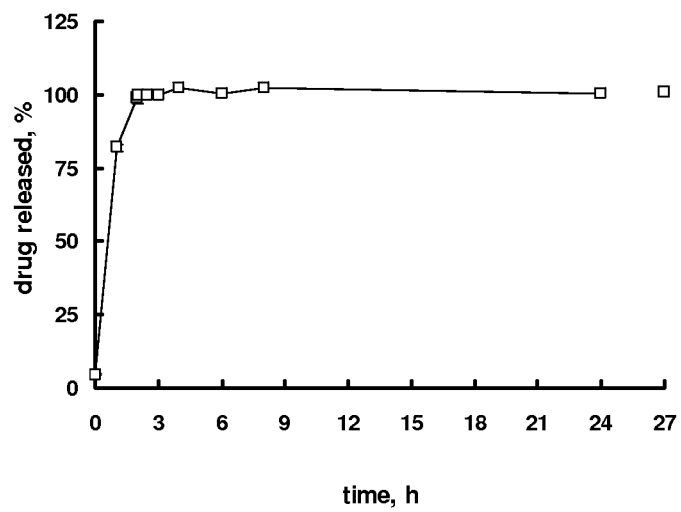
FIG. 14: Bemiparin release profile from tablets prepared according to Example 8 (compound presenting quaternary ammonium groups (Eudragit® L)/glycosaminoglycan. (Bemiparin)=400 mg/200 mg). Results are expressed as weight percent of bemiparin released from tablets as a function of time.

Bemiparin release profile from tablets obtained in this example is shown FIG. 14. Results are expressed as % Bemiparin released from tablets as function of time.

As can be seen in the figure, Eudragit® L does not avoid rapid diffusion of Bemiparin through the polymer. This is probably due to the relatively high percentage of Bemiparin in the polymer which helps formation of pores in the structure of the insoluble Eudragit® L polymer.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 15:
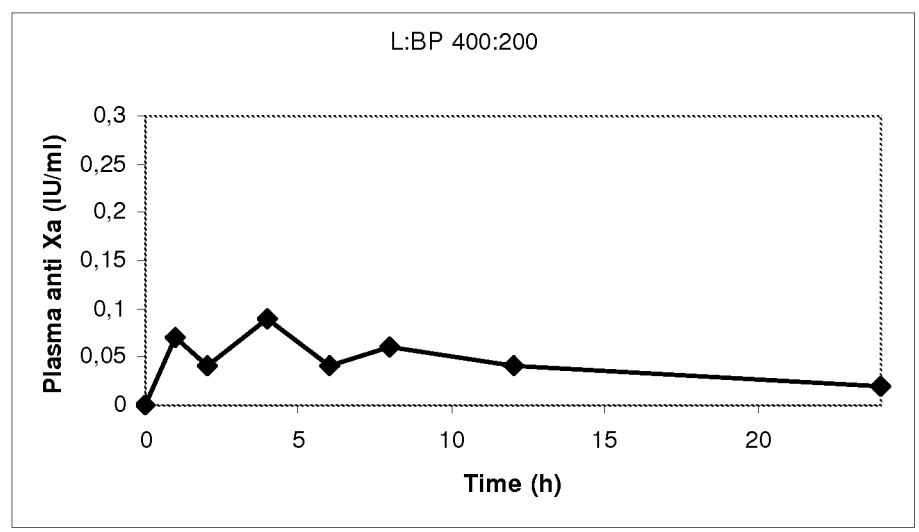
FIG. 15: Plasma anti Xa activity in Beagle dogs after oral administration of 20,000 IU Bemiparin tablets prepared according to Example 8.

Oral administration of 20000 IU Bemiparin in tablets to Beagle dogs resulted in detectable plasma levels as shown in FIG. 15.

As we can see in example 6 to 8, different types of polymers have been tested in order to determine the influence of the amount of charges and the nature of the charged compound GAG mucosal absorption (all these polymers have similar chemical structures but different ammonium proportions). In all the assays GAG/polymer ratio is 1:2.

FIGS. 11, 13 and 15 represented plasma activity values obtained when Eudragit® RL, Eudragit® E and Eudragit® L are tested, respectively.

Eudragit® RL (approx. 0.4 μmol ammonium units/mg formulation) gives the best results reaching a plasma activity of 0.35 UI/ml.

Eudragit® E (approx. 2.12 μmol ammonium units/mg formulation) gives a poor plasma activity reaching the maximum value at 0.06 IU/ml.

Eudragit® L, a polymer without ammonium groups, gives the worst results with poor absorption (0.09 IU/ml) and irregular levels.

To sum up these results we can conclude that the best ammonium proportion for our pharmaceutical formulation should be below 2 μmol ammonium units/mg formulation.

Example 9

Bemiparin Minitablets

Bemiparin minitablets were obtained by direct compression of ingredients in powder by using a 2 mm diameter punch in a minitablet press. Composition of the powder mixture, per minitablet, was the following:

| Ingredient | Amount (mg) |
| --- | --- |
| Eudragit ® RS PO | 5 |
| Bemiparin | 2.5 |
| Mg Stearate | 0.05 |
| Fumed silica | 0.05 |

This Eudragit® RS proportion gives rise to a range of 0.173-0.261 (approximately mean of 0.21) μmol ammonium units per milligram of formulation. Ammonium unit was considered as the ammonium methacrylate monomer present on Eudragit® RSPO and not as its hydrochloride salt.

Humidity content of the present minitablet composition was determined by weight loss on drying at 100° C. during 15 min. The mean value of humidity was 3.44, expressed as (w/w, %).

In Vitro Release Profile:

Bemiparin release from minitablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry.

Figure 16:
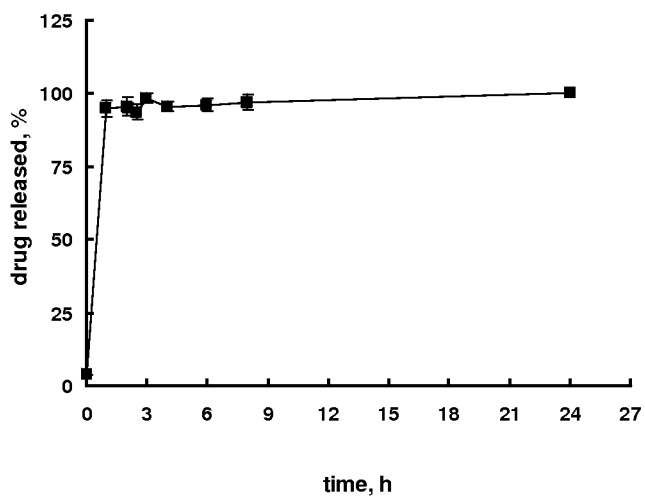
FIG. 16: Bemiparin release profile from tablets prepared according to Example 9 (compound presenting quaternary ammonium groups (Eudragit® RS PO)/glycosaminoglycan (Bemiparin)=5 mg/2.5 mg). Results are expressed as weight percent of bemiparin released from tablets as a function of time.

Bemiparin release profile from minitablets obtained in this example is shown in FIG. 16. Results are expressed as % Bemiparin released from minitablets as function of time.

In Vivo Plasma Levels after Oral Administration to Beagle Dog

Bemiparin minitablets obtained in this example were orally given to Beagle dogs weighing an average of 15 kg. The dose was 20000 IU Bemiparin. Total number of dogs was 3. After oral administration, plasma samples were obtained at 0, 4, 8, 12, 18 and 24 hours and bemiparin absorption was evaluated by measuring plasma anti factor Xa activity in the samples.

Figure 17:
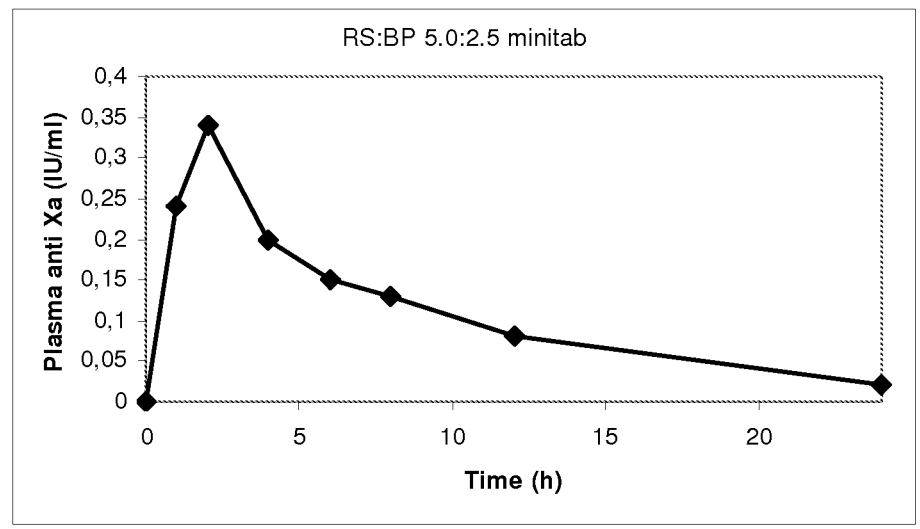
FIG. 17: Plasma anti Xa activity in Beagle dogs after oral administration of 20,000 IU Bemiparin tablets prepared according to Example 9.

Oral administration of 20000 IU Bemiparin in minitablets to Beagle dogs resulted in detectable plasma levels as shown in FIG. 17 (Cmax ~0.35 IU/ml; Tmax ~2.25 hr). This Eudragit® RS proportion gives rise to a approximately 0.21 μmol ammonium units per milligram of formulation.

Example 10

Bemiparin Minitablets

Bemiparin minitablets were obtained by direct compression of ingredients in powder by using a 2 mm diameter punch in a minitablet press. Composition of the powder mixture, per minitablet, was the following:

| Ingredient | Amount (mg) |
| --- | --- |
| Eudragit ® RS PO | 3.75 |
| Bemiparin | 3.75 |
| Mg Stearate | 0.04 |
| Fumed silica | 0.04 |

This Eudragit® RS proportion gives rise to a range of 0.130-0.196 (approximately mean of 0.16) μmol ammonium units per milligram of formulation. Ammonium unit was considered as the ammonium methacrylate monomer present on Eudragit® RSPO and not as its hydrochloride salt.

Humidity content of the tablet corresponding to this example composition was determined by weight loss on drying at 100° C. during 15 min. The mean value of humidity was 2.56, expressed as (w/w, %).

In Vitro Release Profile:

Bemiparin release from minitablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry.

Figure 18:
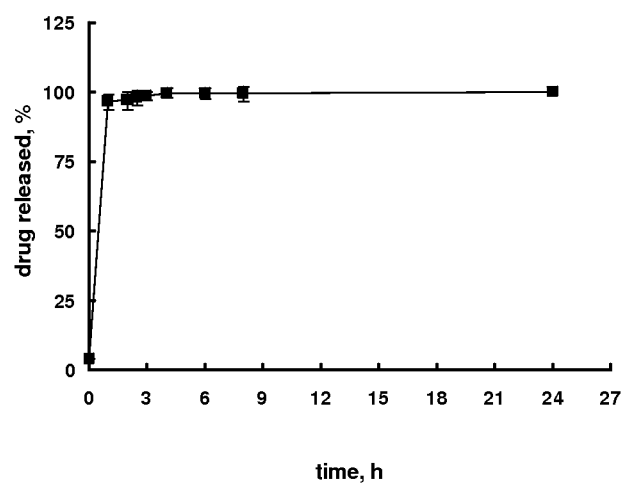
FIG. 18: Bemiparin release profile from tablets prepared according to Example 10 (compound presenting quaternary ammonium groups (Eudragit® RS PO)/glycosaminoglycan (Bemiparin)=3.75 mg/3.75 mg). Results are expressed as weight percent of bemiparin released from tablets as a function of time.

Bemiparin release profile from minitablets obtained in this example is shown in FIG. 18 (results are expressed as % Bemiparin released from minitablets as function of time):

In Vivo Plasma Levels after Oral Administration to Beagle Dog

Bemiparin minitablets obtained in this example were orally given to Beagle dogs weighing an average of 15 kg. The dose was 20000 IU Bemiparin. Total number of dogs was 3. After oral administration, plasma samples were obtained at 0, 4, 8, 12, 18 and 24 hours and bemiparin absorption was evaluated by measuring plasma anti factor Xa activity in the samples.

Figure 19:
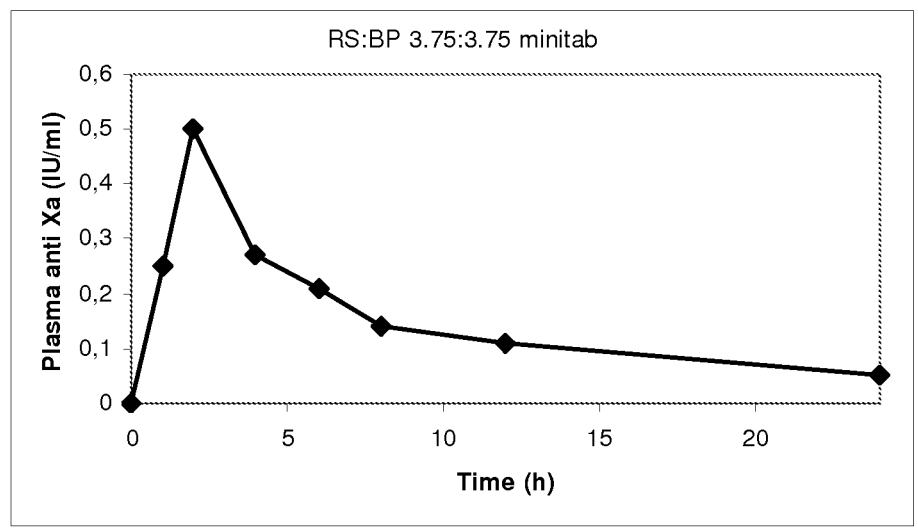
FIG. 19: Plasma anti Xa activity in Beagle dogs after oral administration of 20,000 IU Bemiparin tablets prepared according to Example 10.

Oral administration of 20000 IU Bemiparin in minitablets to Beagle dogs resulted in detectable plasma levels as shown in FIG. 19 (Cmax ~0.5 IU/ml; Tmax ~2 hr).

Example 11

Bemiparin Minitablets

Bemiparin minitablets were obtained by direct compression of ingredients in powder by using a 2 mm diameter punch in a minitablet press. Composition of the powder mixture, per minitablet, was the following:

| Ingredient | Amount (mg) |
| --- | --- |
| Eudragit ® RS PO | 6.0 |
| Bemiparin | 1.5 |
| Mg Stearate | 0.04 |
| Fumed silica | 0.04 |

This Eudragit® RSPO proportion gives rise to a range of 0.207-0.313 (approximately mean of 0.26) μmol ammonium units per milligram of formulation. Ammonium unit was considered as the ammonium methacrylate monomer present on Eudragit® RSPO and not as its hydrochloride salt.

Humidity content of the present minitablet composition was determined by weight loss on drying at 100° C. during 15 min. The mean value of humidity was 3.79, expressed as (w/w, %).

In Vitro Release Profile:

Bemiparin release from minitablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h minitablets were disintegrated in the release medium with a homogenizer and the whole content remained 10 min to determine maximum release of Bemiparin from the sample. In order to clearly represent this value in the graph the data point has been plotted at 27 h.

Figure 20:
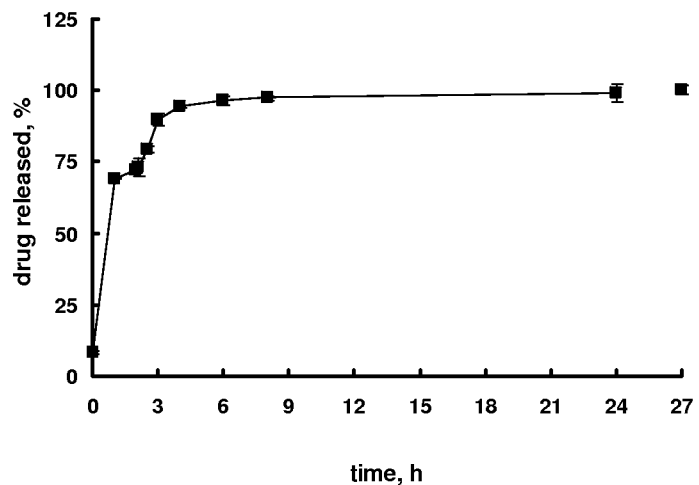
FIG. 20: Bemiparin release profile from tablets prepared according to Example 11 (compound presenting quaternary ammonium groups (Eudragit® RS PO)/glycosaminoglycan (Bemiparin)=6.0 mg/1.5 mg). Results are expressed as weight percent of bemiparin released from tablets as a function of time.

Bemiparin release profile from minitablets obtained in this example is shown in FIG. 20. Results are expressed as % Bemiparin released from minitablets as function of time.

In Vivo Plasma Levels after Oral Administration to Beagle Dog

Bemiparin minitablets obtained in this example were orally given to Beagle dogs weighing an average of 15 kg. The dose was 20000 IU Bemiparin. Total number of dogs was 3. After oral administration, plasma samples were obtained at 0, 4, 8, 12, 18 and 24 hours and bemiparin absorption was evaluated by measuring plasma anti factor Xa activity in the samples.

Figure 21:
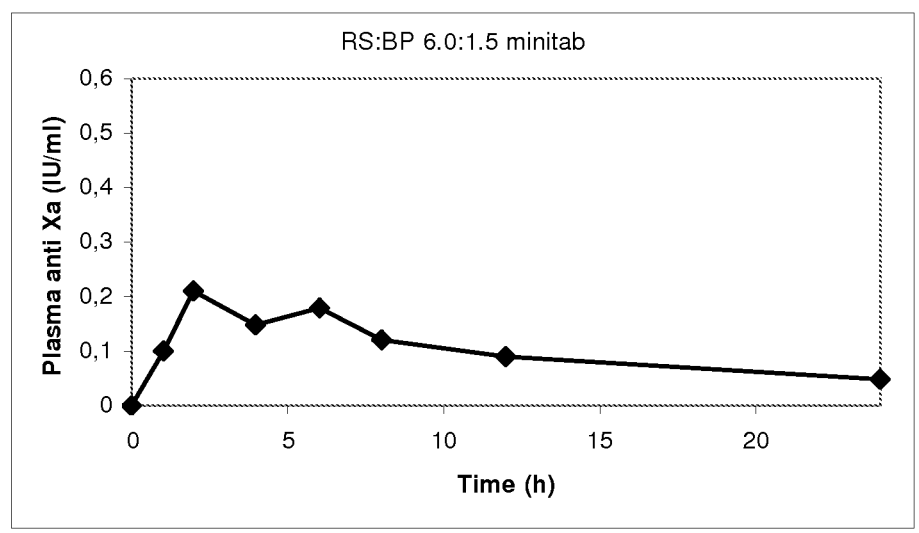
FIG. 21: Plasma anti Xa activity in Beagle dogs after oral administration of 20,000 IU Bemiparin tablets prepared according to Example 11.

Oral administration of 20000 IU Bemiparin in minitablets to Beagle dogs resulted in detectable plasma levels as shown in FIG. 21.

As we can see in examples 9 to 11 with the same polymer (Eudragit® RS), GAG to polymers ratios have been tested in order to elucidated which proportion provides better mucosal absorption Bemiparin:Eudragit 1:4 ratio (see example 11; (Cmax ~0.2 IU/ml; Tmax ~2 hr) results in a absorption of the compound with a plasma levels over to 0.2 IU/ml. However, 1:2 and 1:1 ratios (see examples 9 to 10) results in a good mucosal absorption, with a maximum plasma levels since 0.35 UI/ml to 0.5 UI/ml.

In connection with examples 1 to 5 (tablets), for our pharmaceutical form 1:1 and 1:2 ratios (see examples 1, 3, 6, 9 and 10) are preferred because results in a good mucosal absorption, with a plasma levels over 0.20 UI/ml.

Therefore, for our pharmaceutical form, the percentage of GAG in the formulation is between 20% to 50% w/w.

Example 12

Fondaparinux Minitablets

Fondaparinux minitablets were obtained by direct compression of ingredients in powder by using a 2 mm diameter punch in a minitablet press. Composition of the powder mixture, per minitablet, was the following:

| Ingredient | 12A Amount (mg) | 12B Amount (mg) | 12C Amount (mg) | 12D Amount (mg) |
| --- | --- | --- | --- | --- |
| Fondaparinux | 2.5 | 2.5 | 2.5 | 2.5 |
| Eudragit ® RSPO | 5.0 | | | |
| Mg stearate | 0.04 | 0.04 | 0.04 | 0.04 |
| Microcrystalline cellulose | | 4.5 | 4.4 | 1.2 |
| Lysine | | 0.5 | | |
| Arginine | | | 0.6 | |
| Albumin | | | | 3.8 |

In Vivo Plasma Levels after Intragastric Administration to Wistar Rats

Fondaparinux minitablets obtained in this example were intragastrically given to Wistar rats weighing an average of 300 g. The dose was 2.5 mg Fondaparinux. Total number of rats was 6. After intragastric administration, plasma samples were obtained at 0, 0.5, 1, 2 and 4 hours and Fondapainux absorption was evaluated by measuring plasma anti factor Xa activity in the samples. Results are expressed as mg/L Fondaparinux in plasma.

Figure 22:
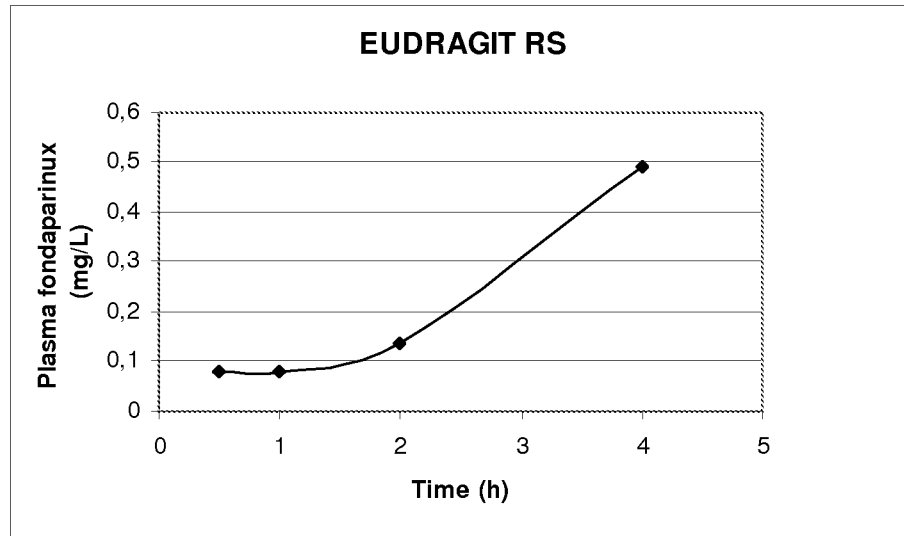
FIG. 22: Plasma anti Xa activity in wistar rats after intragastric administration of minitablets containing 2.5 mg of Fondaparinux as GAG, and 5 mg of Eudragit RS PO as compounds presenting quaternary ammonium groups attached to a non water soluble scaffold prepared according to Example 12.

Intragastric administration of 2.5 mg Fondaparinux in minitablets (12A) to Wistar rats resulted in detectable plasma levels as shown in FIG. 22.

Plasma anti Xa activity in Wistar rats after intragastric administration of 2.5 mg fondaparinux tablets obtained in this example (glycosaminoglycan (fondaparinux)/compound presenting quaternary ammonium groups (Eudragit® RSPO) =2.5 mg/5.0 mg). This Eudragit® RSPO proportion gives rise to an approximately mean of 0.22 μmol ammonium units per milligram of formulation.

This example has been carried out to check if a compound containing ammonium groups attached to a non water soluble scaffold can improved mucosal oral absorption of a glycosaminoglycan (GAG).

Eudragit® RS was selected has a good candidate due to its cationic nature (this polymer contains trimethylated ammonium groups) and absence of water solubility. A priori, trimethyl ammonium groups also seem to be a good choice since distance between sulfate groups in the GAG studied is long enough to fit them (3.5 Å).

Results (mini-tablets 12A) are expressed as mg/L Fondaparinux in plasma.

Comparator formulation 12B provided a fondaparinux maximum plasma level of 0.18 mg/L. Comparator formulation 12C provided a fondaparinux maximum plasma level of 0.14 mg/L. Comparator formulation 12D provided a fondaparinux maximum plasma level of 0.28 mg/L. EUDRAGIT® RSPO provided significantly better results than comparator formulations (12B, 12C and 12D) since fondaparinux peak plasma levels reach 0.5 mg/L in four hours for formulation 12A, which is according to the invention.

Comparative Example 13

Bemiparin in Eudragit® RS Dispersion

A Bemiparin formulation in Eudragit® RS dispersion was prepared as follows. First, the required amount of Bemiparin and Eudragit® RS was dissolved in water. Composition of the formulation, per 200 mg Bemiparin dose, was the following:

| Ingredient | Amount (mg) |
|---|---|
| Bemiparin | 200 |
| Water | 350 |
| Eudragit® RS | 200 |

This Eudragit® RS proportion gives rise to a range of 0.069-0.105 (approximately mean of 0.09) μmol ammonium units per milligram of formulation.

This example has been carried out to check if a non solid matrix pharmaceutical form can improve mucosal oral absorption of a glycosaminoglycan (GAG).

As can be observed, same composition regarding GAG and polymer nature and quantities formulated as a solid matrix (tablets and minitablets) reached plasma levels over 0.3 UI/ml. On the other hand, example 13 formulation presented as a non solid form resulted in plasma levels below 0.1 UI/ml.

The presence of ammonium charges on the surface of a solid form improve GAG oral absorption. The GAG oral absorption is also improved for the fact that these ammoniums are located in an structured scaffold, which seems to be a key point to notably improve GAG oral absorption.

In Vivo Plasma Levels after Oral Administration to Beagle Dogs

Bemiparin formulations obtained in this example were orally given to Beagle dogs weighing an average of 15 kg. The dose was 20000 IU Bemiparin per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 23:
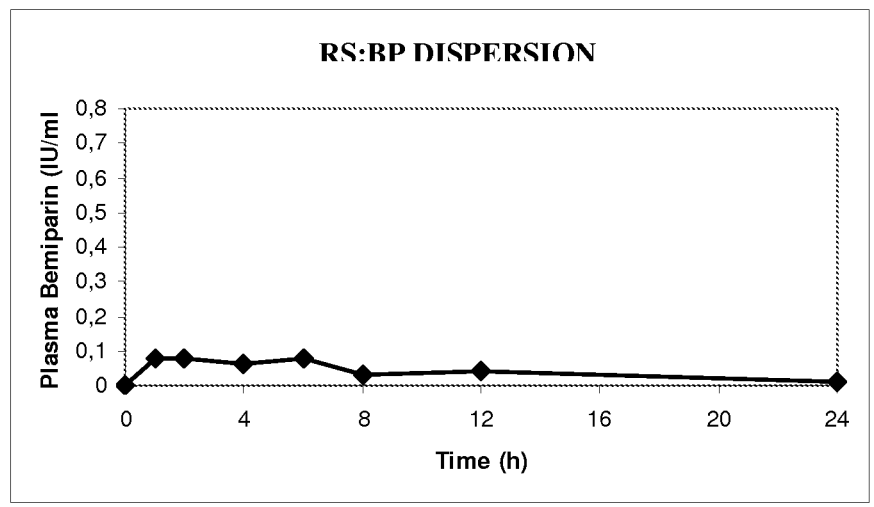
FIG. 23: Plasma anti Xa activity in Beagle dogs after oral administration of 20,000 IU Bemiparin in Eudragit RS dispersion prepared according to comparative Example 13.

Oral administration of 20000 IU Bemiparin in a formulation according to this example to Beagle dogs resulted in very low plasma levels as shown in FIG. 23. This Eudragit® RS proportion gives rise to a approximately 0.1 μmol ammonium units per milligram of formulation.

This example has been carried out to check if a non solid matrix pharmaceutical form can improve mucosal oral absorption of a glycosaminoglycan (GAG).

As can be observed, same composition regarding GAG and polymer nature and quantities (see example 3 and 10) formulated as a solid matrix (tablets and minitablets) reached plasma levels over 0.3 UI/ml. On the other hand, example 13 formulation presented as a non solid form resulted in plasma levels below 0.1 UI/ml.

Example 14

Bemiparin Tablets

Bemiparin tablets were obtained by direct compression of ingredients in powder by using a single punch tablet press. Composition of the powder mixture, per tablet, was the following:

| Ingredient | Amount (mg) |
|---|---|
| Eudragit® RS PO | 400 |
| Bemiparin | 200 |
| Mg Stearate | 3 |

This Eudragit® RSPO proportion gives rise to a range of 0.207-0.313 (approximately mean of 0.26) μmol ammonium units per milligram of formulation Ammonium unit was considered as the ammonium methacrylate monomer present on Eudragit® RSPO and not as its hydrochloride salt.

Humidity content of the tablet corresponding to this example composition was determined by weight loss on drying at 100° C. during 15 min. The mean value of humidity was 12.07, expressed as (w/w, %).

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 24:
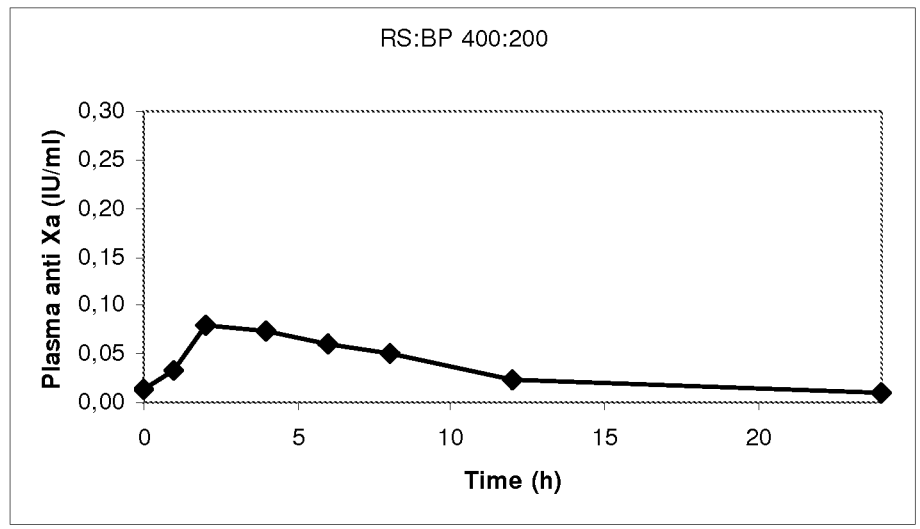
FIG. 24: Plasma anti Xa activity in Beagle dogs after oral administration of 20,000 IU Bemiparin in Eudragit RS tablets prepared according to Example 14.

Oral administration of 20000 IU Bemiparin in tablets to Beagle dogs resulted in detectable plasma levels below to 0.1 IU/ml at all sampling points as shown in FIG. 24.

As we can see in example 2, a composition with a same GAG to polymer ratio and presence of ammonium groups (expressed as μmol/mg of formulation) than in example 16, but with different humidity (w/w, %), has been tested in order to elucidated an influence of this parameter on mucosal absorption. Same composition with a humidity of 5.79% (FIG. 3, example 2) results in a good mucosal absorption with plasma levels over 0.20, whereas that composition with a humidity content of 12.07% results in a poor absorption of the compound with a plasma levels below to 0.1 IU/ml at all sampling points. Hence, different compositions described on example 1 to 4, and 9 to 11, all of then corresponding to humidity contents values in range 2.56-7.85% elicit substantial GAG mucosal absorption with plasma levels over 0.15 IU/ml.

To sum up these results we can conclude that the best humidity content for our pharmaceutical formulation should be below 12% (w/w).

Example 15

Enoxaparin Tablets

Enoxaparin tablets were obtained by direct compression of ingredients in powder by using a 10 mm diameter punch in a single punch tablet press. Composition of the powder mixture, per tablet, was the following:

| Ingredient | Amount (mg) |
|---|---|
| Eudragit® RS PO | 400 |
| Enoxaparin | 200 |
| Mg Stearate | 3 |

This Eudragit® RSPO proportion give, rise to a range of 0.173-0.261 (approximately mean of 0.21) μmol ammonium units per milligram of formulation. Ammonium unit was considered as the ammonium methacrylate monomer present on Eudragit® RSPO and not as its hydrochloride salt.

In Vitro Release Profile:

Enoxaparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Enoxaparin amount present was determined by nephelometry. After 24 h tablets were disintegrated in the release medium with a homogenizer and the whole content remained 10 min to determine maximum release of Enoxaparin from the sample. In order to clearly represent this value in the graph the data point has been plotted at 27 h.

Figure 25:
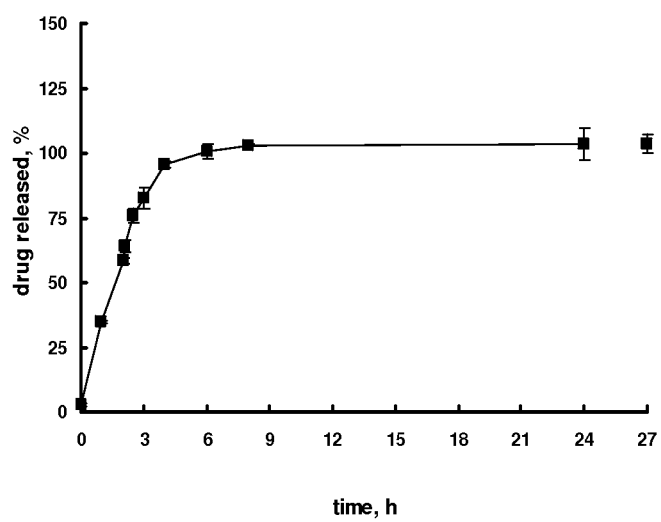
FIG. 25: Enoxaparin release profile from tablets prepared according to Example 15 (compound presenting quaternary ammonium groups (Eudragit® RS PO)/glycosaminoglycan (Enoxaparin)=400 mg/200 mg) Results are expressed as weight percent of enoxaparin released from tablets as a function of time.

Enoxaparin release profile from tablets obtained in this example is shown in FIG. 25. Results are expressed as % Enoxaparin released from tablets as function of time.

In Vivo Plasma Levels after Oral Administration to Beagle Dog

Enoxaparin tablets obtained in this example were orally given to Beagle dogs weighing an average of 15 kg. The dose was 20000 IU Enoxaparin that corresponded to one single tablet per animal. Total number of dogs was 3. After oral administration, plasma samples were obtained at 0, 4, 8, 12, 18 and 24 hours and Enoxaparin absorption was evaluated by measuring plasma anti factor Xa activity in the samples.

Figure 26:
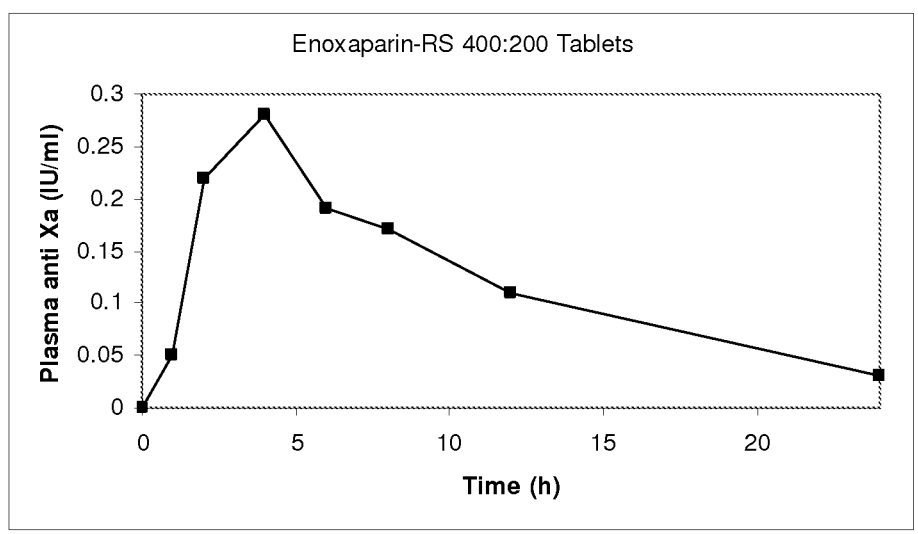
FIG. 26: Plasma anti Xa activity in Beagle dogs after oral administration of 20,000 IU Enoxaparin tablets prepared according to Example 15.

Oral administration of 20000 IU Enoxaparin in tablets to Beagle dogs resulted in good mucosal absorption reaching peak plasma levels of 0.28 IU/ml (FIG. 26) at a Tmax of about 4 hrs.

Example 16

Enoxaparin Tablets

Enoxaparin tablets were obtained by direct compression of ingredients in powder by using a 10 mm diameter punch in a single punch tablet press. Composition of the powder mixture, per tablet, was the following:

| Ingredient | Amount (mg) |
| --- | --- |
| Eudragit ® RS PO | 200 |
| Enoxaparin | 200 |
| Mg Stearate | 2 |

This Eudragit® RSPO proportion gives rise to a range of 0.130-0.196 (approximately mean of 0.16) μmol ammonium units per milligram of formulation. Ammonium unit was considered as the ammonium methacrylate monomer present on Eudragit® RSPO and not as its hydrochloride salt.

In Vitro Release Profile:

Enoxaparin release from tablets was evaluated in USP paddle apparatus (Vankel VK 300, Vankel Industries, Edison, N.J., USA) at 37° C., 0.100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Enoxaparin amount present was determined by nephelometry. After 24 h tablets were disintegrated in the release medium with a homogenizer and the whole content remained 10 min to determine maximum release of Enoxaparin from the sample. In order to clearly represent this value in the graph the data point has been plotted at 27 h.

Figure 27:
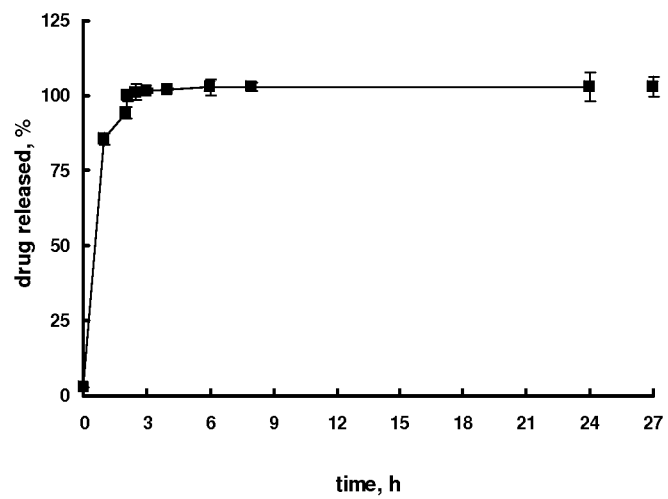
FIG. 27: Enoxaparin release profile from tablets prepared according to Example 16 (compound presenting quaternary ammonium groups (Eudragit® RS PO)/glycosaminoglycan (Enoxaparin)=200 mg/200 mg). Results are expressed as weight percent of enoxaparin released from tablets as a function of time.

Enoxaparin release profile from tablets obtained in this example is shown in FIG. 27. Results are expressed as % Enoxaparin released from tablets as function of time.

In Vivo Plasma Levels after Oral Administration to Beagle Dog

Enoxaparin tablets obtained in this example were orally given to Beagle dogs weighing an average of 15 kg. The dose was 20000 IU Enoxaparin that corresponded to one single tablet per animal. Total number of dogs was 3. After oral administration, plasma samples were obtained at 0, 4, 8, 12, 18 and 24 hours and enoxaparin absorption was evaluated by measuring plasma anti factor Xa activity in the samples.

Figure 28:
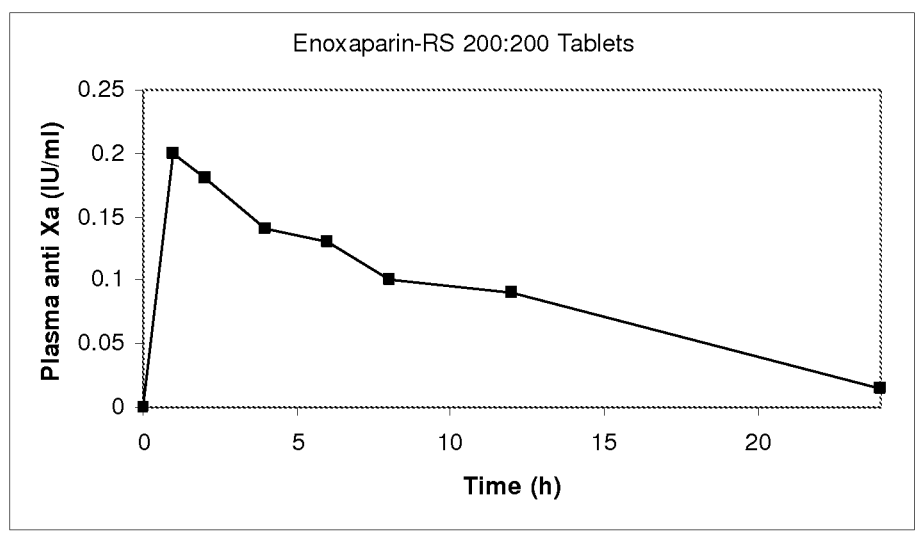
FIG. 28: Plasma anti Xa activity in Beagle dogs after oral administration of 20,000 IU Enoxaparin tablets prepared according to Example 16.

Oral administration of 20000 IU Enoxaparin in tablets to Beagle dogs resulted in peak plasma levels up to 0.2 IU/ml as shown in FIG. 28 at a Tmax of about 1 hr.

Example 17

Enoxaparin Minitablets

Enoxaparin minitablets were obtained by direct compression of ingredients in powder by using a 2 mm diameter punch in a minitablet press. Composition of the powder mixture, per minitablet, was the following:

| Ingredient | Amount (mg) |
| --- | --- |
| Eudragit ® RS PO | 5 |
| Enoxaparin | 2.5 |
| Mg Stearate | 0.05 |
| Fumed silica | 0.05 |

This Eudragit® RS proportion gives rise to a range of 0.173-0.261 (approximately mean of 0.21) μmol ammonium units per milligram of formulation. Ammonium unit was considered as the ammonium methacrylate monomer present on Eudragit® RSPO and not as its hydrochloride salt.

In Vitro Release Profile:

Enoxaparin release from minitablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Enoxaparin amount present was determined by nephelometry.

Figure 29:
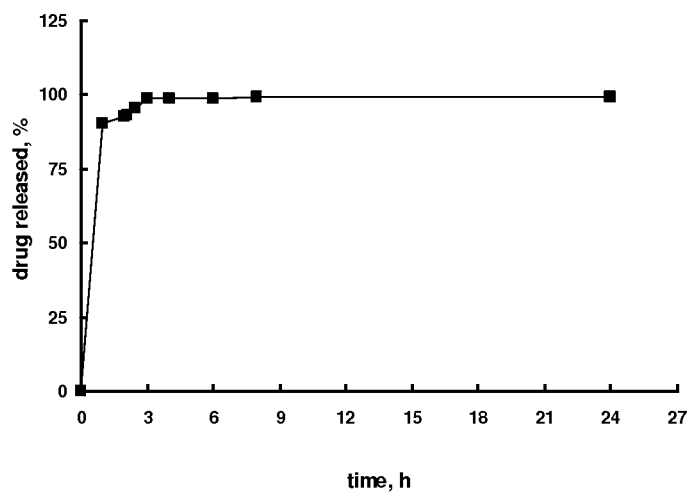
FIG. 29: Enoxaparin release profile from tablets prepared according to Example 17 (compound presenting quaternary ammonium groups (Eudragit® RS PO)/glycosaminoglycan (Enoxaparin)=5 mg/2.5 mg). Results are expressed as weight percent of enoxaparin released from tablets as a function of time.

Enoxaparin release profile from minitablets obtained in this example is shown in FIG. 29. Results are expressed as % Enoxaparin released from minitablets as function of time.

In Vivo Plasma Levels after Oral Administration to Beagle Dog

Enoxaparin minitablets obtained in this example were orally given to Beagle dogs weighing an average of 15 kg. The dose was 20000 IU Enoxaparin. Total number of dogs was 3. After oral administration, plasma samples were obtained at 0, 4, 8, 12, 18 and 24 hours and enoxaparin absorption was evaluated by measuring plasma anti factor Xa activity in the samples.

Figure 30:
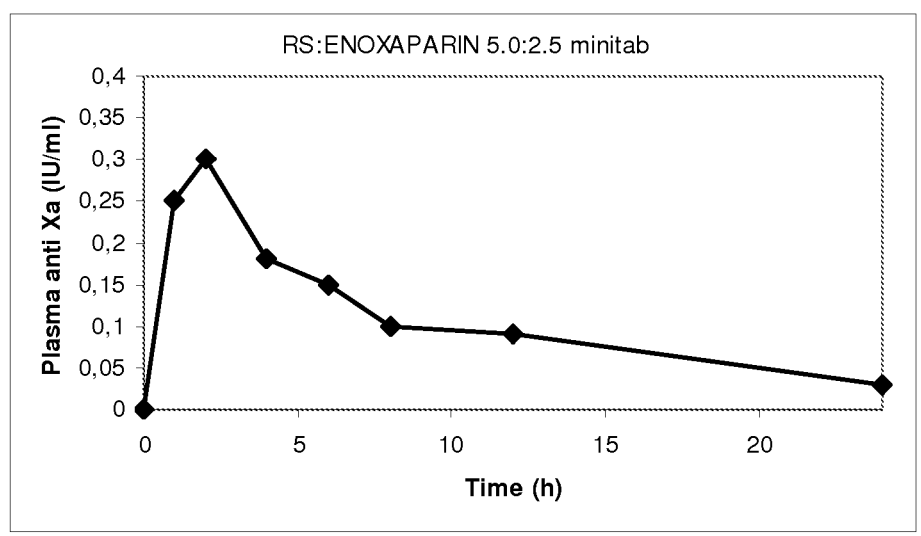
FIG. 30: Plasma anti Xa activity in Beagle dogs after oral administration of 20,000 IU Enoxaparin tablets prepared according to Example 17.

Oral administration of 20000 IU Enoxaparin in minitablets to Beagle dogs resulted in good enoxaparin mucosal absorption with peak plasma levels up to 0.3 IU/ml as shown in FIG. 30 at a Tmax of about 2 hrs.

Example 18

Enoxaparin Minitablets

Enoxaparin minitablets were obtained by direct compression of ingredients in powder by using a 2 mm diameter punch in a minitablet press. Composition of the powder mixture, per minitablet, was the following:

| Ingredient | Amount (mg) |
|---|---|
| Eudragit ® RS PO | 3.75 |
| Enoxaparin | 3.75 |
| Mg Stearate | 0.04 |
| Fumed silica | 0.04 |

This Eudragit® RSPO proportion gives rise to a range of 0.130-0.196 (approximately mean of 0.16) μmol ammonium units per milligram of formulation. Ammonium unit was considered as the ammonium methacrylate monomer present on Eudragit® RSPO and not as its hydrochloride salt.

In Vitro Release Profile:

Enoxaparin release from minitablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Enoxaparin amount present was determined by nephelometry.

Figure 31:
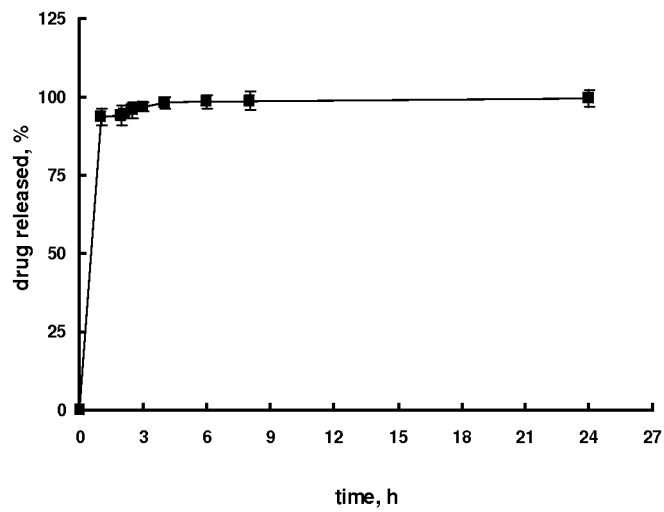
FIG. 31: Enoxaparin release profile from tablets prepared according to Example 18 (compound presenting quaternary ammonium groups (Eudragit® RS PO)/glycosaminoglycan (Enoxaparin)=3.75 mg/3.75 mg). Results are expressed as weight percent of enoxaparin released from tablets as a function of time.

Enoxaparin release profile from minitablets obtained in this example is shown in FIG. 31 (results are expressed as % Enoxaparin released from minitablets as function of time):

In Vivo Plasma Levels after Oral Administration to Beagle Dog

Enoxaparin minitablets obtained in this example were orally given to Beagle dogs weighing an average of 15 kg. The dose was 20000 IU Enoxaparin. Total number of dogs was 3. After oral administration, plasma samples were obtained at 0, 4, 8, 12, 18 and 24 hours and enoxaparin absorption was evaluated by measuring plasma anti factor Xa activity in the samples.

Figure 32:
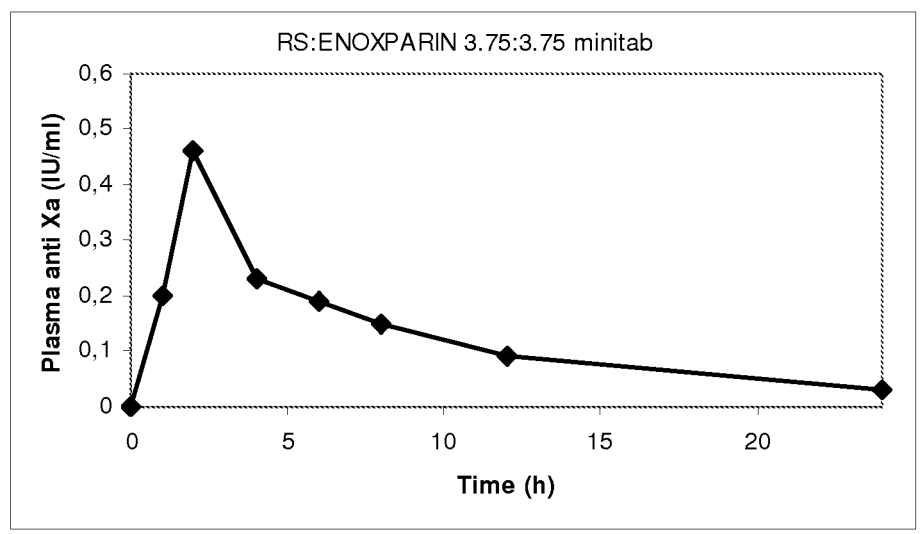
FIG. 32: Plasma anti Xa activity in Beagle dogs after oral administration of 20,000 IU Enoxaparin tablets prepared according to Example 18.

Oral administration of 20000 IU Enoxaparin in minitablets to Beagle dogs resulted in good compound absorption with peak plasma levels over 0.45 IU/ml (FIG. 32) at a Tmax of about 2 hrs.

Example 19

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
|---|---|
| Eudragit ® RS PO | 400 |
| Bemiparin | 200 |

This Eudragit® RSPO proportion gives rise to a range of 0.174-0.262 (approximately mean of 0.22) μmol ammonium units per milligram of formulation. Ammonium unit was considered as the ammonium methacrylate monomer present on Eudragit® RSPO and not as its hydrochloride salt.

Humidity content of the present tablet composition was determined by weight loss on drying at 100° C. during 15 min. The mean value of humidity was 4.03, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 33:
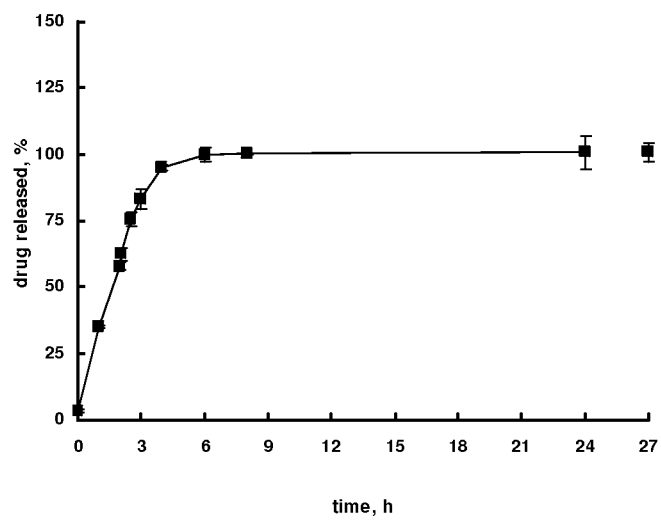
FIG. 33: Bemiparin release profile from tablets prepared according to Example 19 (compound presenting quaternary ammonium groups (Eudragit® RS PO)/glycosaminoglycan (Bemiparin)=400 mg/200 mg). Results are expressed as weight percent of bemiparin released from tablets as a function of time.

Bemiparin release profile from tablets obtained in this example is shown in FIG. 33. Results are expressed as % Bemiparin released from tablets as function of time.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 34:
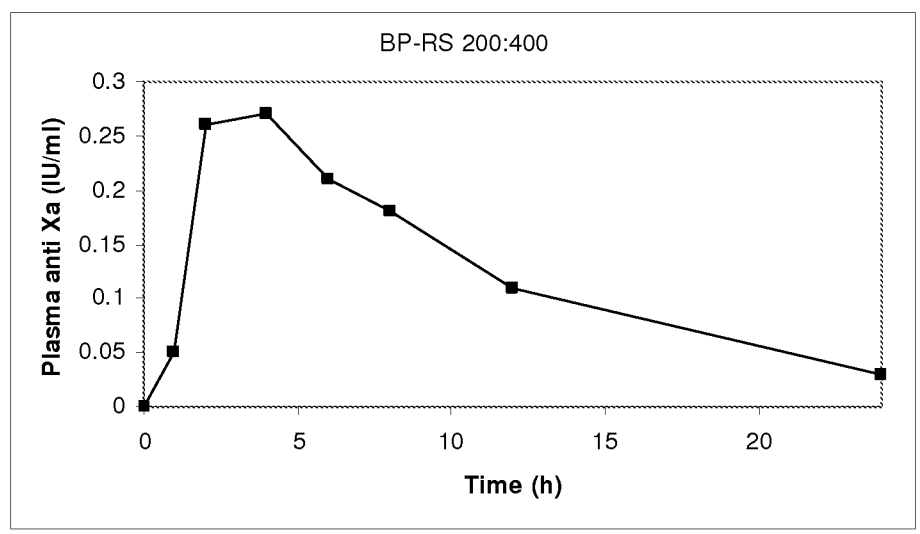
FIG. 34: Plasma anti Xa activity in Beagle dogs after oral administration of 20,000 IU Bemiparin tablets prepared according to Example 19.

Oral administration of 20000 IU Bemiparin in tablets to Beagle dogs resulted in good compound absorption with peak plasma levels over 0.2 IU/ml (FIG. 34) at a Tmax of about 4 hrs.

Example 20

Bemiparin Tablets

Bemiparin tablets were obtained by direct compression of ingredients in powder by using a 10 mm diameter punch in a single punch tablet press. Composition of the powder mixture, per tablet, was the following:

| Ingredient | Amount (mg) |
|---|---|
| Eudragit ® RS PO | 160 |
| Eudragit ® E | 410 |
| Bemiparin | 200 |
| Dispersantt | 24 |
| Mg Stearate | 4 |

This Eudragit® RSPO and Eudragit® E proportion gives rise to a range of 1.536-1.899-(approximately mean of 1.72) μmol ammonium units per milligram of formulation. Ammonium unit was considered as the ammonium methacrylate monomer present on Eudragit® RSPO and not as its hydrochloride salt, and as dimethylaminoethyl groups for Eudragit® E.

Humidity content of the present tablet composition was determined by weight loss on drying at 100° C. during 15 min. The mean value of humidity was 5.13, expressed as (w/w, %).

In Vitro Release Profile:

Bemiparin release from tablets was evaluated in USP paddle apparatus (Vankel VK 300, Vankel Industries, Edison, N.J., USA) at 37° C., 100 rpm, n=2. Release medium was 750 ml 0.1 N HCl for 2 h followed by addition of 225 ml of 0.2M trisodium phosphate to adjust pH=6.8. At previously scheduled time points (1 h, 2 h, 2 h 5 min, 2 h 30 min, 3 h, 4 h, 6 h, 8 h and 24 h) 3 ml were collected and Bemiparin amount present was determined by nephelometry. After 24 h tablets were disintegrated in the release medium with a homogenizer and the whole content remained 10 min to determine maximum release of Bemiparin from the sample. In order to clearly represent this value in the graph the data point has been plotted at 27 h.

Figure 35:
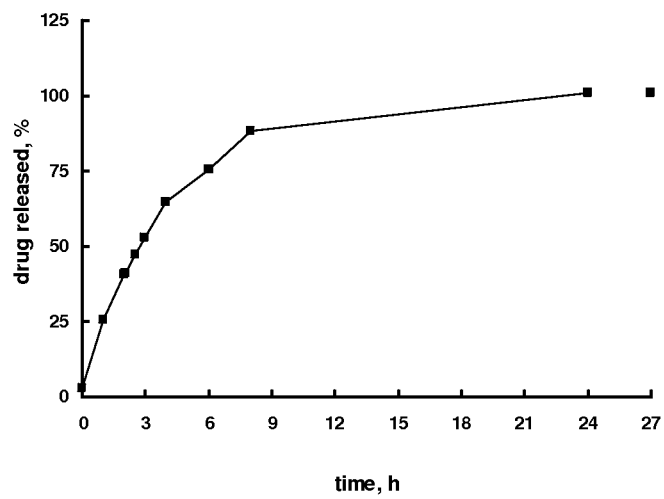
FIG. 35: Bemiparin release profile from tablets prepared according to Example 20 (compound presenting quaternary ammonium groups (Eudragit® RS PO/Eudragit E)/glycosaminoglycan (Bemiparin)=160 mg/410 mg/200 mg). Results are expressed as weight percent of bemiparin released from tablets as a function of time.

Bemiparin release profile from tablets obtained in this example is shown in FIG. 35. Results are expressed as % Bemiparin released from tablets as function of time.

In Vivo Plasma Levels after Oral Administration to Beagle Dog

Bemiparin tablets obtained in this example were orally given to Beagle dogs weighing an average of 15 kg. The dose was 20000 IU Bemiparin that corresponded to one single tablet per animal. Total number of dogs was 3. After oral administration, plasma samples were obtained at 0, 4, 8, 12, 18 and 24 hours and bemiparin absorption was evaluated by measuring plasma anti factor Xa activity in the samples.

Figure 36:
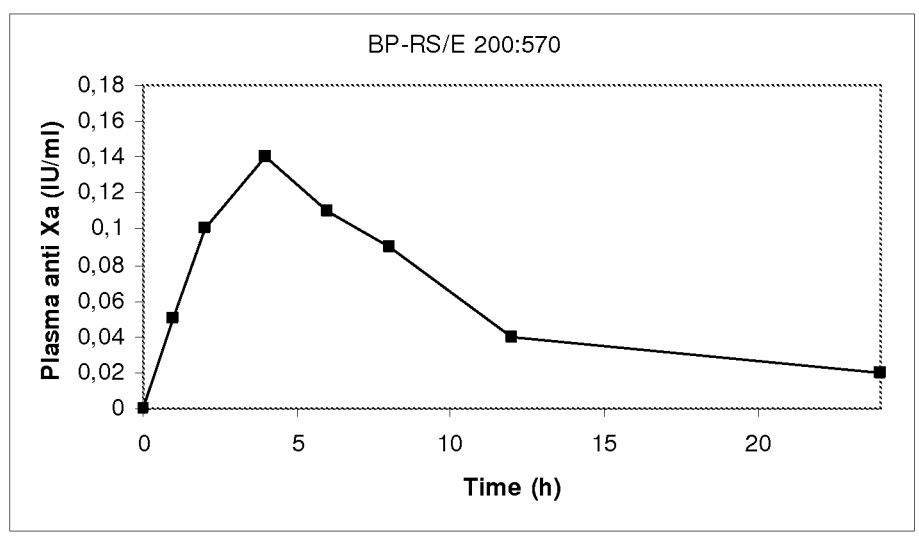
FIG. 36: Plasma anti Xa activity in Beagle dogs after oral administration of 20,000 IU Bemiparin tablets prepared according to Example 20.

Oral administration of 20000 IU Bemiparin in tablets to Beagle dogs resulted in moderate compound absorption with peak plasma levels between 0.1-0.2 IU/ml (FIG. 36) at a Tmax of about 4 hrs.

As used herein, the terms "about" or "approximately" are taken to mean±10%, ±5%, ±2.5% or ±1% of a specified valued. As used herein, the term "substantially" is taken to mean "to a large degree" or "at least a majority of" or "more than 50% of".

Whenever a range is specified herein, the range is intended to include the values at each end of range as well as all values within the range.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A pharmaceutical form comprising a glycosaminoglycan with anions and a compound presenting cations of pH independent quaternary ammonium groups, which compound is a structure of polymers and copolymers derived from acrylic and methacrylic acids esters, wherein:
the proportion of ammonium groups in the pharmaceutical form is between 0.01 to 2.0 µmol ammonium/mg pharmaceutical form,
the proportion of glycosaminoglycan in the pharmaceutical form is between 15% to 50% w/w, and
the pharmaceutical form presents a humidity percentage (w/w) lower than 10%,
wherein the anions of the glycosaminoglycan are only partially neutralized with the cations.

2. The pharmaceutical form according to claim 1 wherein the compound presenting cations of pH independent quaternary ammonium groups is a non-water soluble compound.

3. The pharmaceutical form according to claim 1, wherein the proportion of ammonium groups in the pharmaceutical form is between 0.05-1.7 µmol ammonium/mg pharmaceutical form.

4. The pharmaceutical form according to claim 3 wherein the proportion of ammonium groups in the pharmaceutical form is between 0.16-1.0 µmol ammonium/mg pharmaceutical form.

5. The pharmaceutical form according to claim 4, wherein the proportion of ammonium groups in the pharmaceutical form is between 0.21-0.4 µmol ammonium/mg pharmaceutical form.

6. The pharmaceutical form according to claim 1, wherein the proportion of glycosaminoglycan in the pharmaceutical form is between 20-50% w/w.

7. The pharmaceutical form according to claim 6 wherein the proportion of glycosaminoglycan in the pharmaceutical form is between 25-50% w/w.

8. The pharmaceutical form according to claim 7, wherein the proportion of glycosaminoglycan in the pharmaceutical form is between 33-50% w/w.

9. The pharmaceutical form according to claim 1, wherein the pharmaceutical form presents a humidity percentage (w/w) lower than 8%.

10. The pharmaceutical form according to claim 9, wherein the pharmaceutical form presents a humidity percentage (w/w) lower than 5%.

11. The pharmaceutical form according to claim 1, wherein,
the proportion of ammonium groups in the pharmaceutical form is between from about 0.16 to 1.7 µmol ammonium/mg pharmaceutical composition, and
the proportion of glycosaminoglycan in the pharmaceutical composition is from 20% to 50% w/w.

12. The pharmaceutical form according to claim 1, wherein,
the proportion of ammonium groups in the pharmaceutical form is between from about 0.21 to 0.4 µmol ammonium/mg pharmaceutical composition, and
the proportion of glycosaminoglycan in the pharmaceutical composition is typically from 33% to 50% w/w.

13. The pharmaceutical form according to claim 1, wherein the glycosaminoglycan is selected from the group consisting of unfractionated heparin, low molecular weight heparin, ultralow molecular weight heparin, chondroitin, dermatan and fondaparinux and its pharmaceutically acceptable salts.

14. The pharmaceutical form according to claim 1 further comprising pharmaceutically acceptable excipients.

15. A pharmaceutical formulation comprising the pharmaceutical form as defined in claim 14, wherein the compound presenting cations of quaternary ammonium groups forms part of the surface of said formulation.

16. The pharmaceutical formulation according to claim 14, wherein the percentage (w/w) of excipients or carriers in the formulation is equal or lower than 10%.

17. The pharmaceutical formulation according to claim 14, wherein said formulation is a pellet, a granule, a tablet or a minitablet.

18. The pharmaceutical formulation according to claim 14, wherein said formulation is for administration by oral route.

19. The pharmaceutical formulation according to claim 18, wherein said formulation is not an extended release formulation.

20. The pharmaceutical formulation according to claim 14, wherein the pharmaceutical formulation is applicable to a mucosa selected from oropharyngeal mucosa, gastrointestinal mucosa, pulmonary mucosa, nasal mucosa and vaginal mucosa.

21. A solid pharmaceutical dosage form comprising a compressed composition consisting essentially of an admixture of:
15%-50% wt. of polyanionic sulfated glycosaminoglycan comprising anionic sulfate groups; and 85%-50% wt. of polycationic copolymer of acrylic acid ester and methacrylic acid ester comprising cationic pH independent quaternary ammonium groups; wherein the compressed composition has a moisture content of about 10% wt. or less; and the mole ratio of sulfate groups to ammonium groups in the composition is greater than one, whereby less than the total of sulfate groups of the glycosaminoglycan are neutralized by or complexed with the total of ammonium groups present.

22. The dosage form of claim 21, wherein the compressed composition excludes each of or one or more of a biodegradable polymer, additional counterion substance, rate-controlling coating, surfactant, lipid, bile acid, bile acid salt, bile acid ester, fatty acid, fatty acid salt, fatty ester, fatty ether, hyaluronic acid, and hyaluronic acid salt, said exclusion being independently selected upon each occurrence.

23. The dosage form of claim 21, wherein the compressed composition is a monolithic matrix composition with the glycosaminoglycan dispersed throughout the matrix.

24. The dosage form of claim 21, wherein the weight ratio of glycosaminoglycan to cationic polymer is in the range of 1:1 to 1:4.

25. The dosage form of claim 21, wherein the molar content of ammonium groups in the composition ranges from 0.1 to 3.0 micromoles of ammonium groups per mg of composition.

26. The dosage form of claim 21, wherein the molar content of sulfate groups in the composition ranges from 0.2 to 2.5 micromoles of sulfate groups per mg of composition.

27. The dosage form of claim 21, wherein the molar ratio of ammonium groups to sulfate groups is in the range of 5:95 to 48.1:51.5.

28. The dosage form of claim 21, wherein the percentage of sulfate groups complexed with or neutralized by the ammonium groups is in the range of 5-95%.

29. A solid pharmaceutical dosage form comprising a compressed composition consisting essentially of an admixture of:

15%-50% wt. of polyanionic sulfated glycosaminoglycan comprising anionic sulfate groups; and 85%-50% wt. of polycationic copolymer of acrylic acid ester and methacrylic acid ester comprising cationic pH independent quaternary ammonium groups; wherein the compressed composition has a moisture content of about 10% wt. or less; and the weight ratio of glycosaminoglycan to cationic polymer is in the range of 1:1 to 1:4;

the molar content of ammonium groups in the composition ranges from 0.1 to 3.0 micromoles of ammonium groups per mg of composition;

the molar content of sulfate groups in the composition ranges from 0.2 to 2.5 micromoles of sulfate groups per mg of composition;

the mole ratio of ammonium groups to sulfate groups is in the range of 5:95 to 48.1-51.5, and the percentage of sulfate groups complexed with or neutralized by the ammonium groups is in the range of 5-95%.

30. The dosage form of claim 21, wherein the dosage form is adapted to initiate an extended release of glycosaminoglycan immediately after administration to a subject and to complete the extended release in about 12 hours or less after administration to the subject, or the dosage form is adapted to initiate an extended release of glycosaminoglycan within about 30 min after administration to a subject and to complete the extended release in about 6 hours or less after administration to the subject.

31. The dosage form of claim 21, wherein the glycosaminoglycan is selected from the group consisting of unfractionated heparin, low molecular weight heparin, ultralow molecular weight heparin, chondroitin sulfate, dermatan sulfate, fondaparinux, bemiparin, enoxaparin, tinzaparin, dalteparin, keratan sulfate, parnaparin, reviparin, nadroparin, certoparin, ardeparin and pharmaceutically acceptable salts thereof.

32. The dosage form of claim 21, wherein the compressed composition comprises a combination of two different polycationic copolymers: a first polycationic copolymer comprising cationic pH independent quaternary ammonium groups and a second polycationic copolymer comprising protonated primary amine, secondary amine or tertiary ammonium groups.

33. The dosage form of claim 32, wherein the first polycationic copolymer is selected from the group consisting of: a copolymer of trimethylammonioethyl methacrylate and ethyl methacrylate or methyl methacrylate; a copolymer of trimethylammonioethyl methacrylate, ethyl acrylate and methyl methacrylate; a copolymer of trimethylammonioethyl methacrylate and ethyl acrylate or methyl acrylate; and a combination thereof; and the second polycationic copolymer is selected from the groups consisting of a copolymer of dimethylaminoethyl methacrylate and ethyl methacrylate or methyl methacrylate; a copolymer of dimethylaminoethyl methacrylate, ethyl acrylate and methyl methacrylate; a copolymer of dimethylaminoethyl methacrylate and ethyl acrylate or methyl acrylate; a copolymer of butyl methacrylate and (2-dimethylaminoethyl)-methacrylate and methyl methacrylate; and a combination thereof.

34. The dosage form of claim 32, wherein the first polycationic copolymer is selected from the group consisting of poly(ethyl acrylate-co-methyl methacrylate-co-trimethylammonioethyl methacrylate chloride) 1:2:0.2, and poly(ethyl acrylate-co-methyl methacrylate-co-trimethylammonioethyl methacrylate chloride) 1:2:0.1, and a combination thereof; and the second polycationic polymer is poly(butyl methacrylate-co-dimethylaminoethyl methacrylate-co-methyl methacrylate-) 1:2:1.

35. The dosage form of claim 21, wherein the dosage form is adapted for oral, nasal, pulmonary, vaginal or buccal administration so as to deliver GAG drug to the oropharyngeal mucosa, gastrointestinal mucosa, pulmonary mucosa, nasal mucosa, buccal mucosa or vaginal mucosa.

36. The dosage form of claim 21, wherein:
the proportion of ammonium groups in the compressed composition is about 0.01 to about 2 μmol ammonium/mg compressed composition and the proportion of glycosaminoglycan in the composition is about 15% to about 50% wt.

37. The dosage form of claim 21, wherein the proportion of ammonium groups in the composition is about 0.01 to about 2 μmol ammonium groups/mg composition.

38. The dosage form of claim 21, wherein the dosage form consists essentially of or consists of the compressed composition.

39. The dosage form of claim 21, wherein the proportion of glycosaminoglycan in the composition is about 15 to about 50% w/w.

40. The dosage form of claim 21, wherein the proportion of copolymer present in the composition is about 85 to about 50% w/w.

41. The dosage form of claim 21, wherein the compressed composition comprises a mixture of two, three, four or more different polycationic copolymers.

42. The dosage form of claim 21, wherein the percentage (w/w) of pharmaceutically excipients in the dosage form, other than the polycationic compound/copolymer, is less than or equal to 10% wt. based upon the weight of the dosage form, or the dosage form excludes all pharmaceutically acceptable excipients other than the polycationic compound/copolymer.

43. The dosage form of claim 21, wherein the compressed composition excludes all pharmaceutically acceptable excipients other than the polycationic copolymer.

44. The dosage form of claim 21, wherein the dosage form consists essentially of at least 90% wt. of compressed composition, based upon the weight of the dosage form.

45. The dosage form of claim 21, wherein the compressed composition consists essentially of: a) 85-50% wt. polycationic copolymer, 15-50% wt. glycosaminoglycan, 0.01-1% wt. lubricant and has a moisture content of 10% wt or less; b) 85-50% wt. polycationic copolymer, 15-50% wt. glycosaminoglycan, 0.01-1% wt. lubricant, 0.01-1% wt. glidant and has a moisture content of 10% wt or less; or c) 85-50% wt. polycationic copolymer, 15-50% wt. glycosaminoglycan, 0.01-1% wt. lubricant, 0.01-5% wt. dispersant and has a moisture content of 10% wt or less.

46. The dosage form of claim 21 wherein the proportion of ammonium groups in the compressed composition is about 0.21 to about 0.4 µmol ammonium/mg compressed composition and the proportion of glycosaminoglycan in the composition is about 33% to 50% wt.

47. The dosage form of claim 21, wherein the proportion of ammonium groups in the compressed composition is about 0.16 to about 1.7 µmol ammonium/mg compressed composition and the proportion of glycosaminoglycan in the composition is about 20% to about 50% wt.

48. The dosage form of claim 21, wherein the proportion of ammonium groups in the composition is about 0.05 to about 1.7 µmol ammonium groups/mg composition.

49. The dosage form of claim 21, wherein the proportion of ammonium groups in the composition is about 0.16 to about 1.0 µmol ammonium groups/mg composition.

50. The dosage form of claim 21, wherein the proportion of ammonium groups in the composition is about 0.21 to about 0.4 µmol ammonium/mg composition.

51. The dosage form of claim 21, wherein the proportion of copolymer present in the composition is about 80 to about 50% w/w based upon the total weight of the composition.

52. The dosage form of claim 21, wherein the proportion of copolymer present in the composition is about 75 to about 50% w/w based upon the total weight of the composition.

53. The dosage form of claim 21, wherein the proportion of copolymer present in the composition is about 67 to about 50% w/w based upon the total weight of the composition.

54. The dosage form of claim 21, wherein the proportion of glycosaminoglycan in the composition is about 20 to about 50% w/w based upon the total weight of the composition.

55. The dosage form of claim 21, wherein the proportion of glycosaminoglycan in the composition is about 25 to about 50% w/w based upon the total weight of the composition.

56. The dosage form of claim 21, wherein the proportion of glycosaminoglycan in the composition is about 33 to about 50% w/w based upon the total weight of the composition.

57. The dosage form of claim 21, wherein the dosage form consists of at least 90% wt. of compressed composition, based upon the weight of the dosage form.

58. The dosage form of claim 21, wherein the first polycationic copolymer is selected from the group consisting of: a copolymer of trimethylammonioethyl methacrylate and ethyl methacrylate or methyl methacrylate; a copolymer of trimethylammonioethyl methacrylate, ethyl acrylate and methyl methacrylate; a copolymer of trimethylammonioethyl methacrylate and ethyl acrylate or methyl acrylate; and a combination thereof.

59. The dosage form of claim 21, wherein the first polycationic copolymer is selected from the group consisting of: poly(ethyl acrylate-co-methyl methacrylate-co-trimethylammonioethyl methacrylate chloride) 1:2:0.2, and poly(ethyl acrylate-co-methyl methacrylate-co-trimethylammonioethyl methacrylate chloride) 1:2:0.1, and a combination thereof.

60. The pharmaceutical form of claim 1, wherein the compound is selected from the group consisting of: a copolymer of trimethylammonioethyl methacrylate and ethyl methacrylate or methyl methacrylate; a copolymer of trimethylammonioethyl methacrylate, ethyl acrylate and methyl methacrylate; a copolymer of trimethylammonioethyl methacrylate and ethyl acrylate or methyl acrylate; and a combination thereof.

61. The pharmaceutical form of claim 1, wherein the compound is selected from the group consisting of: poly(ethyl acrylate-co-methyl methacrylate-co-trimethylammonioethyl methacrylate chloride) 1:2:0.2, and poly(ethyl acrylate-co-methyl methacrylate-co-trimethylammonioethyl methacrylate chloride) 1:2:0.1, and a combination thereof.

62. The pharmaceutical form of claim 1 comprising a dose of about 20,000 to about 50,000 IU of glycosaminoglycan, wherein the pharmaceutical form provides a plasma Cmax in the range of about 0.15 to about 1 IU of glycosaminoglycan/ml of plasma following administration to a subject in need thereof.

63. The dosage form of claim 21 comprising a dose of about 20,000 to about 50,000 IU of glycosaminoglycan, wherein the dosage form provides a plasma Cmax in the range of about 0.15 to about 1 IU of glycosaminoglycan/ml of plasma following administration to a subject in need thereof.

64. A method of treating a disease or disorder that is therapeutically responsive to glycosaminoglycan comprising: administering to a subject in need thereof a dosage form of claim 21 according to a prescribed dosing regimen to provide a therapeutically effective amount of glycosaminoglycan to the subject.

65. The method of claim 64, wherein the dosage form provides a Tmax, associated with the plasma Cmax of glycosaminoglycan, in the range of about 1 to about 6 hours after administration.

66. The method of claim 64, wherein the dosage form provides a plasma Cmax in the range of about 0.15 to about 1 IU of glycosaminoglycan/ml of plasma following administration to a subject in need thereof when a dose of about 20,000 to about 50,000 IU is administered to a subject in need thereof.

* * * * *